(12) United States Patent
Stevens et al.

(10) Patent No.: US 11,424,011 B2
(45) Date of Patent: Aug. 23, 2022

(54) ANALYZING KNOWLEDGE GRAPHS WITH UNBOUNDED INSIGHT GENERATION

(71) Applicant: International Business Machines Corporation, Armonk, NY (US)

(72) Inventors: Richard J. Stevens, Monkton, VT (US); Fernando Jose Suarez Saiz, Armonk, NY (US); Eric W. Will, Rochester, MN (US); Adam Clark, Mantorville, MN (US)

(73) Assignee: International Business Machines Corporation, Armonk, NY (US)

( * ) Notice: Subject to any disclaimer, the term of this patent is extended or adjusted under 35 U.S.C. 154(b) by 557 days.

(21) Appl. No.: 16/215,280

(22) Filed: Dec. 10, 2018

(65) Prior Publication Data

US 2020/0185066 A1 Jun. 11, 2020

(51) Int. Cl.
*G16H 50/70* (2018.01)
*G16H 10/60* (2018.01)
*G16H 20/00* (2018.01)
*G06F 16/28* (2019.01)
*G06F 16/2457* (2019.01)
(Continued)

(52) U.S. Cl.
CPC ....... *G16H 10/60* (2018.01); *G06F 16/24578* (2019.01); *G06F 16/285* (2019.01); *G06F 16/9024* (2019.01); *G16H 10/20* (2018.01); *G16H 20/00* (2018.01)

(58) Field of Classification Search
CPC ........ G16H 10/60; G16H 20/00; G16H 10/20; G16H 50/70; G16H 50/30; G06F 16/285; G06F 16/24578; G06F 16/9024; G06F 16/313
See application file for complete search history.

(56) References Cited

U.S. PATENT DOCUMENTS

| | | | |
|---|---|---|---|
| 7,809,660 B2 | 10/2010 | Friedlander et al. | |
| 10,095,829 B2* | 10/2018 | Lazar | G16H 50/20 |
| 2014/0244292 A1 | 8/2014 | Rosenberg et al. | |
| 2014/0310016 A1 | 10/2014 | Kenney et al. | |

(Continued)

OTHER PUBLICATIONS

McCusker "Finding melanoma drugs through a probabilistic knowledge graph" Feb. 13, 2017 PeerJ Computer Science (Year: 2017).*

(Continued)

*Primary Examiner* — Eliza A Lam
(74) *Attorney, Agent, or Firm* — Patterson + Sheridan, LLP

(57) ABSTRACT

Techniques for unbounded therapy evaluation are provided. A request to suggest a potential therapy based on a patient profile is received. A plurality of accepted therapies is determined based on the patient profile, where the plurality of accepted therapies is based on stored definitions obtained from one or more subject matter experts. Next, a plurality of therapy components is identified based on the plurality of accepted therapies. A plurality of potential therapies is then identified based on the plurality of therapy components, where none of the plurality of potential therapies are included in the plurality of accepted therapies. A score is generated for a potential therapy of the plurality of potential therapies based on analyzing a knowledge graph, where the score indicates a suitability of the potential therapy for a patient associated with the patient profile. Finally, the potential therapy is provided, along with an indication of the score.

20 Claims, 11 Drawing Sheets

(51) Int. Cl.
*G16H 10/20* (2018.01)
*G06F 16/901* (2019.01)

(56) References Cited

U.S. PATENT DOCUMENTS

| | | | |
|---|---|---|---|
| 2015/0019232 A1* | 1/2015 | Ebadollahi | G16H 20/10 |
| | | | 705/2 |
| 2017/0053540 A1* | 2/2017 | Meagher | G09B 5/00 |
| 2017/0161446 A1 | 6/2017 | Kronander | |
| 2017/0177822 A1 | 6/2017 | Fogel | |
| 2017/0228505 A1 | 8/2017 | Allen et al. | |

OTHER PUBLICATIONS

Shi et al. "Semantic Health Knowledge Graph: Semantic Integration of Heterogeneous Medical Knowledge and Services" BioMed Research International (Year: 2017).*

* cited by examiner

ANALYZING KNOWLEDGE GRAPHS WITH UNBOUNDED INSIGHT GENERATION

BACKGROUND

The present disclosure relates to knowledge graphs, and more specifically, to identifying and scoring unbounded therapies by evaluating a knowledge graph.

In a variety of domains, studies, experiments, and trials are performed to understand how potential options or selections interact and compare to each other. For example, in the medical field, studies and trials are performed to determine the efficacy of new and existing therapies, in order to determine the best practices for treating or curing illnesses or disorders. Frequently, the results of these studies, experiments, and trials are published for review by others. Currently, the published literature is reviewed manually by subject-matter experts (SMEs) to determine the state of the field, and provide guidance with respect to optimal therapies. However, these determinations are time-consuming, expensive, and inherently biased. Further, the published literature is expanding at an increasing and unprecedented rate. As the number of published documents increases, it has become impossible to aggregate and interpret them all. Thus, current guidelines and best practices are universally outdated, and potentially conflict with newly discovered therapies or interactions.

Additionally, when patients are to be treated, healthcare providers rely on a bounded set of therapies that are considered accepted or appropriate, depending on the cohort of the patient and the disorder to be treated. The process to add new therapies to this accepted set is laborious and lengthy. With current advancements in medical treatments, alternative, new, or better treatments are becoming available frequently. However, given the rapid pace and complexity of the published literature, it is impossible for healthcare providers to identify and evaluate these potential therapies. Thus, patient outcomes are often worse than they could be, because the bounded set of therapies cannot expand to consider or include potential new treatment options without significant time and expense.

SUMMARY

According to one embodiment of the present disclosure, a method is provided. The method includes receiving a request to suggest a potential therapy based on a first patient profile, and determining a plurality of accepted therapies based on the first patient profile, wherein the plurality of accepted therapies is based on stored definitions obtained from one or more subject matter experts. The method further includes identifying a plurality of therapy components based on the plurality of accepted therapies, and identifying a plurality of potential therapies based on the plurality of therapy components, wherein none of the plurality of potential therapies are included in the plurality of accepted therapies. Additionally, the method includes generating a first score for a first potential therapy of the plurality of potential therapies based on analyzing a knowledge graph, wherein the first score indicates a suitability of the first potential therapy for a first patient associated with the first patient profile. Finally, the method includes providing the first potential therapy, along with an indication of the first score.

According to a second embodiment of the present disclosure, a computer-readable storage medium is provided. The computer-readable storage medium has computer-readable program code embodied therewith, the computer-readable program code executable by one or more computer processors to perform an operation. The operation includes receiving a request to suggest a potential therapy based on a first patient profile, and determining a plurality of accepted therapies based on the first patient profile, wherein the plurality of accepted therapies is based on stored definitions obtained from one or more subject matter experts. The operation further includes identifying a plurality of therapy components based on the plurality of accepted therapies, and identifying a plurality of potential therapies based on the plurality of therapy components, wherein none of the plurality of potential therapies are included in the plurality of accepted therapies. Additionally, the operation includes generating a first score for a first potential therapy of the plurality of potential therapies based on analyzing a knowledge graph, wherein the first score indicates a suitability of the first potential therapy for a first patient associated with the first patient profile. Finally, the operation includes providing the first potential therapy, along with an indication of the first score.

According to a third embodiment of the present disclosure, a system is provided. The system includes one or more computer processors, and a memory containing a program which when executed by the one or more computer processors performs an operation. The operation includes receiving a request to suggest a potential therapy based on a first patient profile, and determining a plurality of accepted therapies based on the first patient profile, wherein the plurality of accepted therapies is based on stored definitions obtained from one or more subject matter experts. The operation further includes identifying a plurality of therapy components based on the plurality of accepted therapies, and identifying a plurality of potential therapies based on the plurality of therapy components, wherein none of the plurality of potential therapies are included in the plurality of accepted therapies. Additionally, the operation includes generating a first score for a first potential therapy of the plurality of potential therapies based on analyzing a knowledge graph, wherein the first score indicates a suitability of the first potential therapy for a first patient associated with the first patient profile. Finally, the operation includes providing the first potential therapy, along with an indication of the first score.

DETAILED DESCRIPTION

Figure 1:
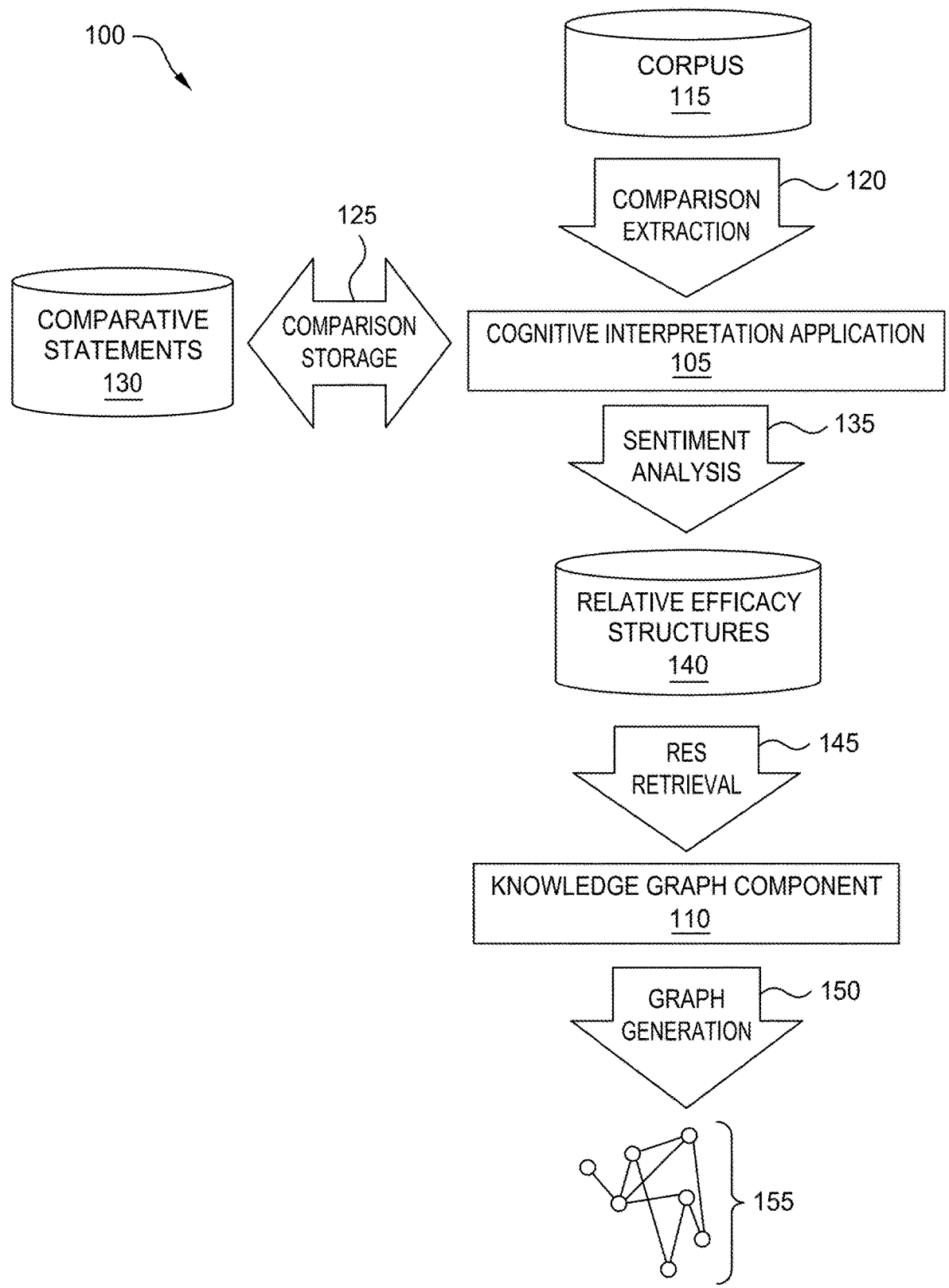
FIG. 1 illustrates a workflow for cognitively determining the relative efficacy of therapies, according to one embodiment disclosed herein.

In embodiments of the present disclosure, potential therapies are identified and evaluated for patients based on information contained in a knowledge graph. In some embodiments, a set of defined or accepted treatments or therapies are identified for a given patient or cohort. In one embodiment, the set of accepted treatments is defined by one or more subject matter experts (SMEs), such as in the medical literature (e.g., by standards-setting bodies) or by an institution (e.g., a hospital or clinic). In one embodiment, the set of accepted therapies is defined based on the practices of a particular SME or group of SMEs. For example, in such an embodiment, the set of accepted therapies can be defined based on therapies that an identified healthcare provider has used or recommended in the past to treat patients included in the cohort.

In one embodiment, the therapies in the set of accepted therapies are evaluated to determine relative efficacies and expected outcomes for patients in the cohort. In some embodiments, rather than limiting suggested therapies to this bounded set, however, additional therapies (e.g., from an unbounded set) can be identified as potential therapies for treating the patient. In an embodiment, these potential therapies are also evaluated to determine their relationship to the bounded set of therapies, and to estimate their potential efficacy for the patient. In this way, patient outcomes are improved because novel therapies can be identified for potential use. Based on these potential new therapies, the healthcare provider can make more informed decisions about up-to-date therapies and comparisons based on a knowledge graph that takes into account new literature as it is produced.

In some embodiments, the potential therapies are classified based on their potential value or use. For example, in one embodiment, potential therapies can include potentially better (or improved) therapies. In one embodiment, a potentially better therapy is one that is found, based on the knowledge graph, to have a positive relationship to at least one therapy in the bounded set (e.g., indicating that it performs better than the therapy in the set), and to have no known negative relationships to any therapies in the bounded set (e.g., indicating that there is no existing evidence indicating that a therapy in the bounded set performs better). In some embodiments, the potential therapies similarly include potential alternative therapies. In one embodiment, a potential alternative therapy is a therapy with at least one positive relationship to one or more therapies in the accepted set, but that may also have negative relationships to therapies in the set. That is, a potential alternative therapy is one that is better than some therapies in the accepted set, and worse than others. In some embodiments, these alternative therapies can be particularly useful for when the better therapies in the bounded set are inapplicable (e.g., because of a contraindication that the patient possesses).

Further, in some embodiments, the potential therapies can include potential new therapies. In an embodiment, a potential new therapy is one that does not have any evidence comparing it to therapies in the bounded set (e.g., it has never been compared directly and cannot be indirectly compared because the knowledge graph lacks such links). However, in an embodiment, the potential new therapy is identified based on literature indicating its expected efficacy or outcomes, which embodiments of the present disclosure can identify and compare to therapies in the set. In an embodiment, before potential therapies can be identified, a knowledge graph must be constructed. In some embodiments, the knowledge graph is generated based on comparative statements (e.g., comparisons between therapies) found in published literature. In one embodiment, the knowledge graph is also built based on non-comparative statements (e.g., statements about the efficacy or outcomes of particular therapies, without any explicit comparison to other therapies).

In some embodiments of the present disclosure, techniques for cognitive analysis, representation, and interpretation of published literature are provided. In one embodiment, a corpus of medical literature is parsed and analyzed to identify and extract comparative statements or opinions made by the authors of the paper. For example, in a conclusion or summary, the authors may indicate that a particular therapy showed improved results, as compared to one or more other therapies (or as compared to the known or popular literature and practices). These conclusions are provided in natural language text, and are rarely structured in a way that allows for easy ingestion of the information. Embodiments of the present disclosure are discussed with reference to medical literature. However, these examples are not limiting on the present disclosure, and one of skill in the art will recognize other domains and literature that the present embodiments can be applied to.

In one embodiment, these comparative statements are interpreted to determine a sentiment of the statement, and the relative efficacy of each therapy discussed. In some embodiments, a data structure, referred to herein as a relative efficacy structure or RES, is generated to capture the natural language comparative statement in a useful format. For example, in one embodiment, the RES has a number of dimensions, including the directionality of the comparison (e.g., which therapy is superior), the magnitude of the difference, the particular outcome the statement refers to (e.g., survival, progression-free survival, remission, etc.), qualifiers of the statement (e.g., limitations or specifications), and the like. In an embodiment, each RES is also associated with a weight, which is based on a variety of factors related to the underlying comparative statement and the nature of the article it is contained in.

In one embodiment, if a comparison is found in one direction (e.g., that treatment A is better than treatment B), a complementary RES is created in the opposite direction (e.g., indicating that treatment B is worse than treatment A). In this way, queries for information for a given treatment or therapy can identify all documents that involve the therapy, regardless of whether the document deemed the therapy to be superior or inferior.

In some embodiments, a knowledge graph can be generated based on the determined relationships extracted from one or more published document. For example, in one embodiment, each node in the knowledge graph corresponds to a particular therapy, and each edge corresponds to one or more RESs. In this way, the knowledge graph can be interrogated or searched to identify optimal treatment options for a given patient, based on a tremendous variety of medical literature. In such an embodiment, patient outcomes are improved, as the current state of the literature can be captured and ingested into the knowledge graph rapidly, reducing or eliminating the need for SME review. Further, in embodiments, the RESs provide additional insight and knowledge that is not accessible or present in existing solutions. Thus, embodiments of the present disclosure enable high-precision searching, and allow users to analyze the literature at a more granular level.

In some embodiments, users can search or query the knowledge graph based on therapies, cohorts, disorders, and the like, to return a subset of the graph that is relevant to the search. Further, in some embodiments, nodes and/or connections can be selected to retrieve a link to any documents or published literature that was analyzed to create the node or edge. In this way, users can readily access the relevant literature, if they wish to investigate further or obtain more information about why the topology of the graph is shaped as it is, as well as why particular connections exist.

Embodiments of the present disclosure can be applied to extract and interpret comparative statements made in any field. In one embodiment, medical literature (e.g., published studies, trials, experiments, and the like) is ingested. In some embodiments, the literature is analyzed to identify comparisons or statements about relative efficacy between therapy options. In an embodiment, a therapy is any treatment used to treat a disorder. As used herein, therapies can include drugs, medications, exercises, surgeries, use of equipment, prescribed activities, and the like. Further, in embodiments, therapies can include refraining from certain activities and withdrawing or reducing treatments. Additionally, in embodiments, a therapy may include multiple treatments or prescribed activities (e.g., multiple medications). As used herein, a medical disorder can include any illness or medical condition, including but not limited to mental or physical disease, sickness, disability, infection, symptoms, conditions, or statuses.

FIG. 1 illustrates a workflow 100 for cognitively determining the relative efficacy of therapies, according to one embodiment disclosed herein. In the illustrated embodiment, a Cognitive Interpretation Application 105 analyzes documents to extract Comparative Statements 130 and generate RESs 140, and a Knowledge Graph Component 110 analyzes these RESs 140 to generate a Knowledge Graph 150. In some embodiments, a Knowledge Graph 150 is generated to aid visualization or understanding of the literature (although it may not actually be displayed). In some embodiments, however, the knowledge graph is not created, and the RESs 140 are used for other purposes. That is, in some embodiments, the generated RESs are usable or searchable by other systems or components, and can be utilized to aid understanding and improve treatment selection, without the construction of a knowledge graph.

In the illustrated workflow 100, the Cognitive Interpretation Application 105 analyzes a Corpus 115 of documents to perform Comparison Extraction 120. In an embodiment, the Corpus 115 includes documents which include at least some portion of natural language text, which may or may not have comparative statements by the author(s). In some embodiments, the Corpus 115 corresponds to a particular domain of interest to a user. For example, in one embodiment, a larger corpus or collection of documents is searched to identify a subset of the documents that relate to a particular disorder, therapy, or set of disorders or therapies. In such an embodiment, this subset of documents makes up the Corpus 115. In some embodiments, the workflow 100 is performed on multiple corpora (e.g., once for each therapy or disorder).

In an embodiment, the Comparison Extraction 120 comprises utilizing one or more natural language processing (NLP) techniques to identify comparative statements in the text included in the Corpus 115. For example, in one embodiment, the Cognitive Interpretation Application 105 searches for comparative language (such as "superior," "better," "worse," "improved," and the like). In some embodiments, the Cognitive Interpretation Application 105 analyzes predefined sections of the documents to identify these comparative statements (e.g., the abstract, conclusion, methods, discussion, etc.). That is, in an embodiment, a user or administrator can specify portions or sections in the documents that should be analyzed. In other embodiments, the Cognitive Interpretation Application 105 analyzes the full text of the document. In one embodiment, the Cognitive Interpretation Application 105 first searches the identified sections (as identified by their headings or by metadata tags), and only parses the rest of the document if the specified section(s) do not include any comparative statements (or if the specified section(s) cannot be found or do not exist in the document).

In some embodiments, the Comparison Extraction 120 also includes remedying unknown terms in the statement, such as through disambiguation and acronym resolution. For example, if the comparative statement includes an acronym, in one embodiment, the Cognitive Interpretation Application 105 can expand the acronym. Similarly, if the statement includes ambiguous or general language (such as, "all treatments studied herein", "with respect to the relevant cohort," or "generic chemotherapy drugs"), the Cognitive Interpretation Application 105 can determine a meaning for the terms. In some embodiments, the Cognitive Interpretation Application 105 first parses the selected document to identify the meaning of the term. That is, the Cognitive Interpretation Application 105 attempts to find meaning for the unknown term by analyzing the text of the document in which the comparative statement was found using NLP techniques. If no satisfactory disambiguation is found (e.g., the confidence level of any potential disambiguations is below a threshold), the Cognitive Interpretation Application 105 can access other literature (or one or more knowledge graphs) to disambiguate the term. In some embodiments, if the true meaning is not found within the corresponding document, the confidence or weight of the extracted comparison is reduced.

In some embodiments, Comparison Extraction 120 includes annotation of the extracted comparative statements. For example, in one embodiment, the Cognitive Interpretation Application 105 utilizes one or more NLP techniques to identify the therapy or therapies involved in the statement, the qualifier or comparative term utilized, and the like. In some embodiments, the Cognitive Interpretation Application 105 also determines the cohort(s) to which the statement(s) apply, as discussed in more detail below. Additionally, in some embodiments, the Cognitive Interpretation Application 105 determines characteristics of the comparative statements, such as where in the text it was located (e.g., which section it was found in), the publication date of the document, whether the document has been peer-reviewed, an identity of the publisher or entity that provided the document, and the like.

In the illustrated embodiment, the Cognitive Interpretation Application 105 stores the extracted comparisons (e.g., the natural language text) in a data store for Comparative Statements 130. In some embodiments, these stored Comparative Statements 130 are annotated to identify the relevant therapies, qualifiers, and the like. In some embodiments, the Comparative Statements 130 also indicate the disorder that is relevant to the comparison. In other embodiments, the disorder is described by the cohort and/or cohort qualifiers. In embodiments, the Comparative Statements 130 can be stored locally by the Cognitive Interpretation Application 105, or in one or more remote storage locations (such as in the cloud). As illustrated, the Cognitive Interpretation Application 105 then performs Sentiment Analysis 135 on the extracted Comparative Statements 130, to generate a set of RESs 140. In an embodiment, this Sentiment Analysis 135 includes classifying each statement as positive, negative, or neutral with respect to each of the implicated therapies. In some embodiments, the Cognitive Interpretation Application 105 also determines a degree of the sentiment (based on, for example, the strength of the language or term used). Further, in some embodiments, the RESs 140 include an indication as to which outcome or outcome type the comparison relates to (e.g., overall survival, progression-free survival, etc.).

In some embodiments, the RESs 140 include an indication as to the therapies involved, the relevant cohort, and the like. In one embodiment, each RES 140 corresponds to a particular Comparative Statement 130. In one embodiment, each RES 140 is weighted based on a variety of factors. For example, in an embodiment, the weighting factors include how recently the corresponding document was published, whether the document has been peer-reviewed, the identity of the publisher or provider for the document, the number of patients evaluated in the clinical study, and the like. In one embodiment, publishers are associated with predefined weights or strengths, based on their prestige or trustworthiness. In some embodiments, the Cognitive Interpretation Application 105 weights each RES 140 based on a confidence level as well. In one embodiment, this confidence level is based in part on a confidence value returned by the NLP models. Further, in an embodiment, the confidence is adjusted based on where in the document the corresponding Comparative Statement 130 was found. For example, a comparison found in the abstract or conclusion can be given a higher weight, while a comparison found elsewhere in the document can be given a lower weight.

In the illustrated embodiment, the Knowledge Graph Component 110 retrieves these RESs 140 from the data store, and performs Graph Generation 150 to generate a Knowledge Graph 155. In an embodiment, each node in the Knowledge Graph 150 is a therapy (or combination of therapies), and each edge is based on the determined relationships and relative efficacies (e.g., the RESs 140). In one embodiment, the Knowledge Graph Component 110 adds an edge or connection for each determined RESs 140 (e.g., for each comparative statement found). In some embodiments, the Knowledge Graph Component 110 aggregates the comparisons. For example, in an embodiment, for each outcome type and cohort combination, the Knowledge Graph Component 110 can aggregate the corresponding RESs 140, in order to determine an overall relative efficacy for the therapies, with respect to the cohort and outcome. In some embodiments, this aggregation is based in part on the weights of each comparison, as discussed above.

Although not depicted in the illustrated embodiment, in some embodiments, the Cognitive Interpretation Application 105 also identifies statements relating to the efficacy or outcomes of a therapy, even in the absence of a comparison between therapies. In such an embodiment, the Cognitive Interpretation Application 105 can also perform Sentiment Analysis 135 on the non-comparative statements to determine whether the therapy is being referred to in a positive, neutral, or negative manner. In some embodiments, the Cognitive Interpretation Application 105 also determines the efficacy and/or outcomes of the therapy, if available in the Corpus 115. For example, in such an embodiment, the Cognitive Interpretation Application 105 can determine what percentages of patients benefitted (with respect to each potential outcome), the magnitude of the benefits, and the like. In an embodiment, the Knowledge Graph Component 110 then incorporates these non-comparative statements into the Knowledge Graph 155 (e.g., by adding or refining a node corresponding to the therapy being discussed).

Figure 2:
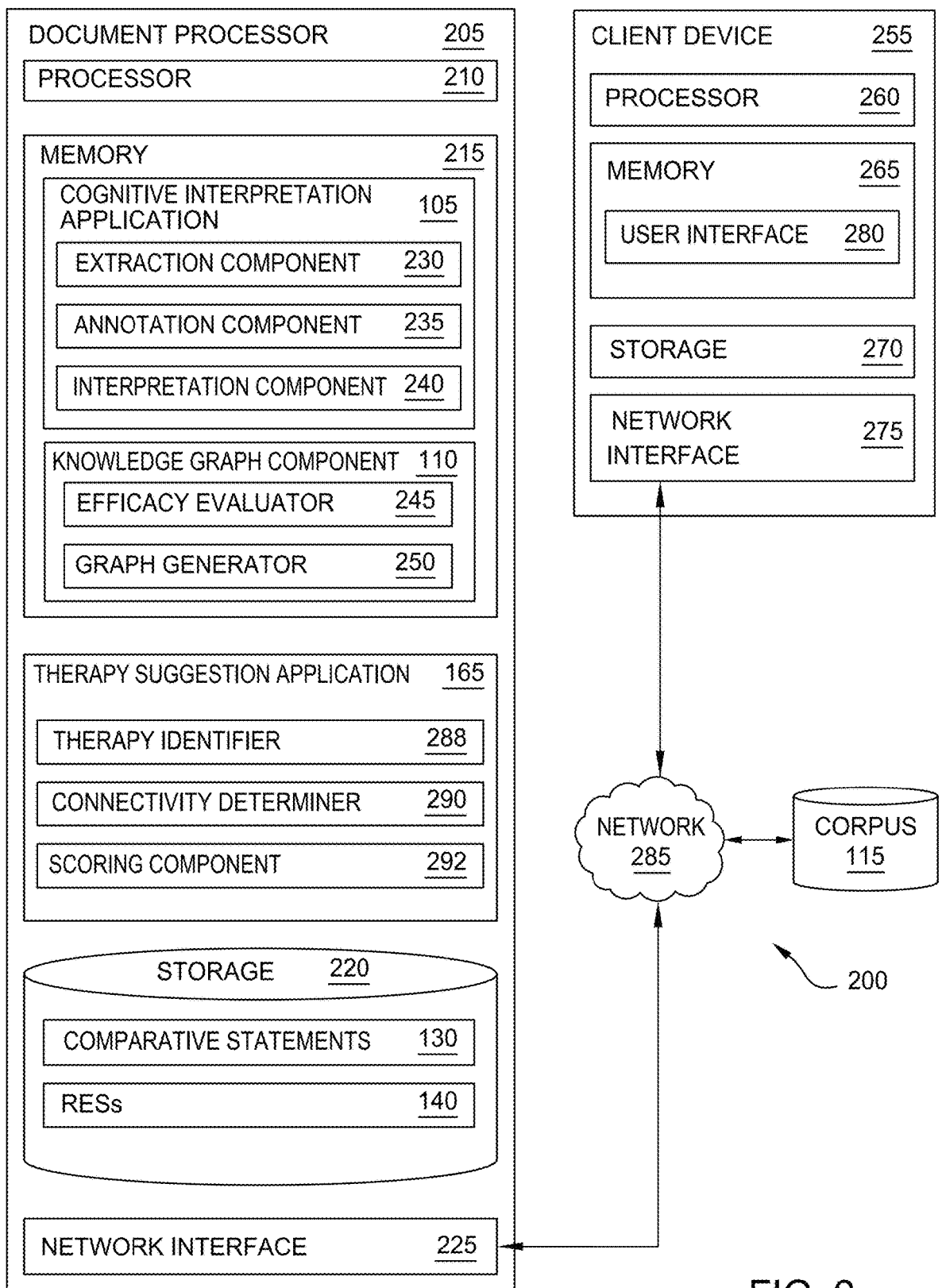
FIG. 2 is a block diagram of a system configured to cognitively determine the relative efficacy of therapies, according to one embodiment disclosed herein.

FIG. 2 is a block diagram of a system 200 configured to cognitively determine the relative efficacy of therapies, according to one embodiment disclosed herein. In the illustrated embodiment, the system 200 includes a Document Processor 205, a Client Device 255, and a Corpus 115. Although illustrated as discrete components, in embodiments, the Document Processor 205, Client Device 255, and Corpus 115 may operate or reside on a single device, or may be distributed across any number of devices. As illustrated, the Document Processor 205, Client Device 255, and Corpus 115 are communicatively linked through a Network 285. In one embodiment, the Network 285 is the Internet. Additionally, though a single Corpus 115 is illustrated, in embodiments, any number of corpora may be analyzed by the Document Processor 205.

As illustrated, the Document Processor 205 includes a Processor 210, a Memory 215, and Storage 220. In the illustrated embodiment, Processor 210 retrieves and executes programming instructions stored in Memory 215 as well as stores and retrieves application data residing in Storage 220. Processor 210 is representative of a single CPU, multiple CPUs, a single CPU having multiple processing cores, and the like. Memory 215 is generally included to be representative of a random access memory. Storage 220 may be a disk drive or flash-based storage device, and may include fixed and/or removable storage devices, such as fixed disk drives, removable memory cards, or optical storage, network attached storage (NAS), or storage area-network (SAN). Via the Network Interface 225, the Document Processor 205 can be communicatively coupled with corpuses of documents (such as Corpus 115), Client Devices 255, and the like.

In the illustrated embodiment, the Storage 220 of the Document Processor 205 includes a set of Comparative Statements 130 and RESs 140. In some embodiments, as discussed above, the Comparative Statements 130 and/or RESs 140 may be stored in one or more remote storage locations, such as in the cloud. Further, in some embodiments, the Storage 220 includes non-comparative statements as well. As discussed above, in an embodiment, the Comparative Statements 130 are annotated natural language text extracts from documents in the Corpus 115. In one embodiment, each Comparative Statement 130 includes a comparison or opinion of the author of the corresponding document. In some embodiments, the annotations indicate the qualifier or comparator used by the author, the therapies implicated by the statement, the cohort or cohort qualifiers that limit the applicability of the comparison, and the like. Further, in some embodiments, the Comparative Statements 130 include publication characteristics of the statements, such as the location in their corresponding documents where they were found, the date of the publication, the entity that published it, and the like. Additionally, in one embodiment, the Comparative Statements 130 include an indication as to the confidence value that the NLP model(s) generated when parsing the statements.

As discussed above, in one embodiment, each RES 140 is a data structure representing a particular Comparative Statement 130. In some embodiments, each RES 140 indicates the therapies involved, the directionality or sentiment of the comparison, the cohort implicated, and the like. Further, in an embodiment, each RES 140 includes a weight, which can be based on a variety of factors including the publication characteristics of the underlying Comparative Statement 130, the confidence of the NLP model(s), and the like. In some embodiments, the RESs 140 are configured to be searchable, such that other systems or components (such as the Knowledge Graph Component 110) can readily access the information, and obtain an up-to-date and comprehensive understanding of the current state of the literature.

In the illustrated embodiment, the Memory 215 of the Document Processor 205 includes a Cognitive Interpretation Application 105, a Knowledge Graph Component 110, and a Therapy Suggestion Application 165. The Cognitive Interpretation Application 105 includes an Extraction Component 230, an Annotation Component 235, and an Interpretation Component 240. Although depicted as discrete components for illustration, in embodiments, the operations and functionality of the Extraction Component 230, Annotation Component 235, and Interpretation Component 240 can be combined or divided across any number of components. Further, although depicted as software components residing in Memory 215, in embodiments, the operations and functionality of the Extraction Component 230, Annotation Component 235, and Interpretation Component 240 can be implemented using hardware, software, or a combination of hardware and software.

In an embodiment, the Extraction Component 230 identifies and extracts statements that include comparisons between therapies or treatment options from documents in the Corpus 115, as discussed above. In some embodiments, the Extraction Component 230 utilizes one or more NLP techniques or models to identify the relevant text. Further, in an embodiment, the Annotation Component 235 annotates the extracted statements. In one embodiment, the Annotation Component 235 utilizes predefined rules, and/or additional NLP models and/or techniques to annotate the statements. These annotated statements are then stored in the Comparative Statements 130. In this way, the textual comparisons found in the Corpus 115 are organized and represented in the Storage 220.

In the illustrated embodiment, the Interpretation Component 240 retrieves these Comparative Statements 130 and performs logical interpretation or sentiment analysis on them. In one embodiment, the Interpretation Component 240 classifies each Comparative Statement 130 as positive, negative, or neutral, with respect to each pair of involved therapies or treatments. For example, if the statement is that "treatment A led to better results than treatment B," the Interpretation Component 240 can determine that the comparison is positive with respect to treatment A, and negative with respect to treatment B. Similarly, if the statement is "treatments C and D were both inferior to treatment E," the Interpretation Component 240 determines that, as between therapies C and D, the sentiment is "neutral" or equal. However, as between treatment E and treatments C and D, the sentiment is positive. In this way, the Interpretation Component 240 determines the efficacy of each therapy, as compared to one or more other therapies in the statement.

In one embodiment, the Interpretation Component 240 also generates RESs 140 based on this analysis, as discussed below in more detail. That is, in an embodiment, the Interpretation Component 240 generates an organized and defined data structure that includes the relevant information from the textual Comparative Statement 130. In some embodiments, the Interpretation Component 240 generates a single RES 140 for each Comparative Statement 130. For example, in such an embodiment, if the sentiment is that treatment A is better than treatment B, the Interpretation Component 240 will generate a RES 140 indicating that treatment A is positive with respect to treatment B. In some embodiments, the Interpretation Component 240 also generates a second RES 140 indicating that treatment B is negative with respect to treatment A.

In the illustrated embodiment, the Knowledge Graph Component 110 generally retrieves the RESs 140 from Storage 220, and generates one or more knowledge graphs. As illustrated, the Knowledge Graph Component 110 includes an Efficacy Evaluator 245, and a Graph Generator 250. Although depicted as discrete components for illustration, in embodiments, the operations and functionality of the Efficacy Evaluator 245 and Graph Generator 250 can be combined or divided across any number of components. Further, although depicted as software components residing in Memory 215, in embodiments, the operations and functionality of the Efficacy Evaluator 245 and Graph Generator 250 can be implemented using hardware, software, or a combination of hardware and software. In an embodiment, the Efficacy Evaluator 245 retrieves and evaluates the RESs 140. For example, in one embodiment, the Efficacy Evaluator 245 searches for RESs 140 relating to one or more disorders or therapies that a user or administrator has selected. In other embodiments, the Efficacy Evaluator 245 retrieves and evaluates all available RESs 140. In an embodiment, the evaluation includes determining whether each RES 140 is already included in the knowledge graph.

Additionally, in some embodiments, the Efficacy Evaluator 245 aggregates the RESs 140 as appropriate, to determine an overall relative efficacy for each set of therapies. For example, in one embodiment, the Efficacy Evaluator 245 identifies RESs 140 with the same endpoints (e.g., that involve the same set of therapies) and aggregates them based on their respective weights to generate an overall relative efficacy between the therapies. In an embodiment, the Graph Generator 250 generates, inserts, and updates or refines nodes and edges in the knowledge graph, based on the evaluation provided by the Efficacy Evaluator 245. In some embodiments, the Graph Generator 250 and/or Efficacy Evaluator 245 aggregate the data by identifying all RESs 140 involving the same pair of therapies and including them in the graph, in order to capture all available evidence that compares the therapies without attempting to establish whether one is overall superior to the other.

In the illustrated embodiment, the Therapy Suggestion Application 165 includes a Therapy Identifier 288, a Connectivity Determiner 290, and a Scoring Component 292. Although depicted as discrete components for illustration, in embodiments, the operations and functionality of the Therapy Identifier 288, Connectivity Determiner 290, and Scoring Component 292 can be combined or divided across any number of components. Further, although depicted as software components residing in Memory 215, in embodiments, the operations and functionality of the Therapy Identifier 288, Connectivity Determiner 290, and Scoring Component 292 can be implemented using hardware, software, or a combination of hardware and software.

In an embodiment, the Therapy Suggestion Application 165 analyzes the knowledge graph to identify and evaluate therapies that may be useful to treat patients. In the illustrated embodiment, the Therapy Identifier 288 receives information relating to one or more patients, and identifies therapies that may be relevant. In one embodiment, the Therapy Identifier 288 receives an indication of a particular patient or patient profile, and determines a corresponding cohort for the patient (e.g., based on attributes of the patient found in the patient profile, electronic medical records (EMRs), or specified by the healthcare provider or patient). In some embodiments, the Therapy Identifier 288 receives an indication of one or more cohorts for analysis.

Once the cohort is identified, in one embodiment, the Therapy Identifier 288 determines a set of defined or accepted therapies to be used to treat patients in the cohort that have the defined disorder or condition. In one embodiment, this includes retrieving the set of accepted therapies that has been previously defined for the cohort. In embodiments, the Therapy Identifier 288 utilizes this bounded set of therapies as a starting point to identify related therapies that are potentially of interest. In one embodiment, the Therapy Identifier 288 analyzes each of the therapies in the accepted set of therapies to identify therapy components of each. For example, in an embodiment, a therapy can include one or more components such as one or more medications, procedures, activities, and the like.

In an embodiment, the Therapy Identifier 288 identifies other therapies that also include one or more of the identified therapy components. In this way, the Therapy Identifier 288 can identify therapies that may be related or similar (to some extent) to the accepted therapies. In some embodiments, this identification is made by analyzing the knowledge graph. In one embodiment, the Therapy Identifier 288 only includes a therapy in the list of potential therapies if the corresponding node in the knowledge graph indicates that it is suitable for the identified cohort (e.g., because at least one published document discusses it being used or tested with the identified cohort).

In some embodiments, the Therapy Identifier 288 also identifies other related therapies that are broader or more specific than the accepted therapies, or that are in the same class. In one embodiment, for a first therapy component in the accepted therapies, the Therapy Identifier 288 identifies a set of therapy components that are more general or broader, in that they each include the accepted therapy component. For example, if the accepted therapy includes a lumpectomy, the Therapy Identifier 288 can identify other therapies that include a mastectomy. Similarly, in one embodiment, for a first therapy component in the accepted therapies, the Therapy Identifier 288 identifies a set of therapy components that are more narrow or specific, in that the accepted therapy component includes the more specific component. For example, if the accepted therapy includes a nonsteroidal anti-inflammatory drug (NSAIDs), the Therapy Identifier 288 can identify other therapies that include specific types or brands of NSAID.

In some embodiment, the Therapy Identifier 288 also identifies other therapy components that are in the same class as the accepted component. For example, if an accepted therapy includes a particular medication, the Therapy Identifier 288 can identify other medications within the same class of drugs, and identify other therapies that include these related medications. In an embodiment, each of these determinations (e.g., more general, more specific, or same class) is performed by analyzing medical literature, or by analyzing one or more knowledge graphs that define the relationships between various therapy components. In one embodiment, the Therapy Identifier 288 can also analyze the knowledge graph to identify one or more new therapies that have do not include any of the accepted components, based on determining that it has nevertheless been used to treat patients in the cohort. In some embodiments, the Therapy Identifier 288 only selects such therapies if the supporting evidence is relatively new (e.g., younger than a defined threshold), which can indicate that the list of accepted therapies has not yet been updated.

In one embodiment, once this set of potential therapies is identified, the Connectivity Determiner 290 parses the knowledge graph to determine whether each is connected to one or more therapies in the accepted set, as discussed below in more detail. If so, the Connectivity Determiner 290 can further determine the nature of that connection (e.g., whether it is direct or indirect through one or more other connections), as discussed below in more detail. In one embodiment, the Connectivity Determiner 290 classifies the therapies based on their connectivity to the accepted set of therapies. In the illustrated embodiment, the Scoring Component 292 then scores and ranks the determined set of therapies (which can include the accepted therapies, as well as unbounded potential therapies) based on a variety of factors. For example, in one embodiment, the Scoring Component 292 scores therapies based on how effective they are expected to be, and their relative efficacy as compared to each other. In some embodiments, the Scoring Component 292 further scores potential therapies based on how similar or different they are from the accepted set of therapies, how closely connected they are in the knowledge graph to one or more accepted therapies, how new the evidence supporting the potential therapy is, and the like.

In the illustrated embodiment, the Client Device 255 includes a Processor 260, a Memory 265, and Storage 270. In the illustrated embodiment, Processor 260 retrieves and executes programming instructions stored in Memory 265 as well as stores and retrieves application data residing in Storage 270. Processor 260 is representative of a single CPU, multiple CPUs, a single CPU having multiple processing cores, and the like. Memory 265 is generally included to be representative of a random access memory. Storage 270 may be a disk drive or flash-based storage device, and may include fixed and/or removable storage devices, such as fixed disk drives, removable memory cards, or optical storage, network attached storage (NAS), or storage area-network (SAN). Via the Network Interface 275, the Client Device 255 can be communicatively coupled with corpuses of documents (such as Corpus 115), Document Processor 205, and the like.

As illustrated, the Memory 265 of the Client Device 255 includes a User Interface 280 for interacting with the Corpus 115 and/or Document Processor 205. In an embodiment, the User Interface 280 includes a graphical user interface (GUI) that lets users or administrators retrieve and review documents in the Corpus 115. In some embodiments, the User Interface 280 also allows the user to select a subset of the Corpus 115 (e.g., via search queries) to be processed by the Document Processor 205.

Although not illustrated, in embodiments, the Cognitive Interpretation Application 105, Knowledge Graph Component 110, and Therapy Suggestion Application 165 each provide one or more application programming interfaces (APIs) that allow the user (through the User Interface 280) to control the operations of the components. For example, in an embodiment, the user can use the User Interface 280 and APIs to indicate the set of documents to be analyzed, and to adjust any settings or configurations of the Cognitive Interpretation Application 105. Further, in an embodiment, the User Interface 280 and APIs enable the user to review the Comparative Statements 130 and/or RESs 140. Additionally, in an embodiment, the User Interface 280 and APIs allow the user to direct the Knowledge Graph Component 110 to generate one or more knowledge graphs based on the RESs 140, and to analyze and parse the generated graphs. Additionally, in an embodiment, the APIs allow the user to search for and receive evaluations for potential therapy options that are not constrained by the bounded set of accepted therapies.

Figure 3A:
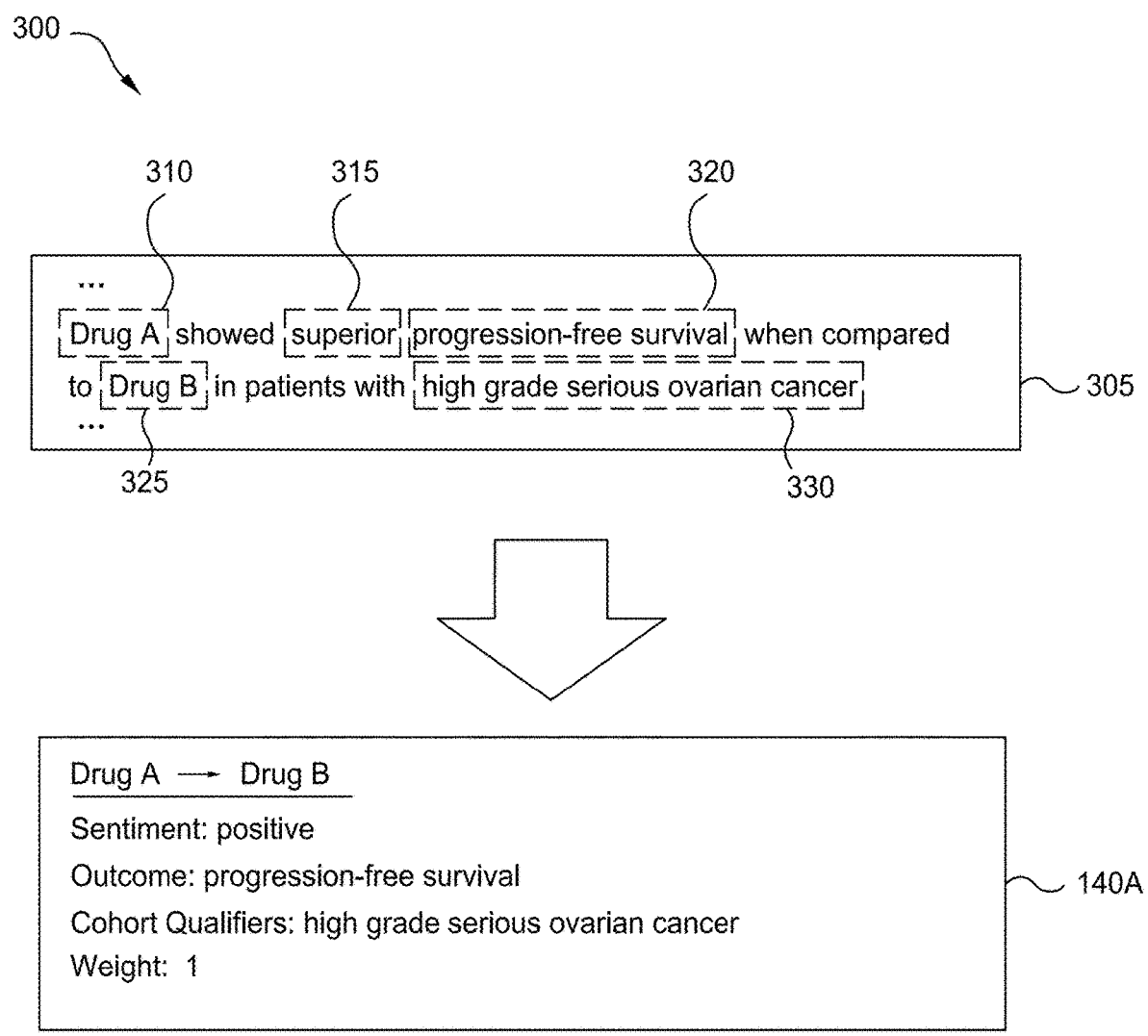
FIG. 3A is a workflow for determining the efficacy for a therapy, as compared to a different therapy, according to one embodiment disclosed herein.

FIG. 3A illustrates a workflow 300 for determining the efficacy for a therapy, as compared to a different therapy, according to one embodiment disclosed herein. In the illustrated workflow 300, a comparative statement (included in an Excerpt 305) is annotated with Annotations 310, 315, 320, 325, and 330. As illustrated by the ellipses above and below the comparative statement, the original document can be any size or length. In an embodiment, the Excerpt 305 was extracted from a document (e.g., by the Extraction Component 230) based on determining that it included a comparative statement.

In the illustrated embodiment, the Excerpt 305 was annotated by the Annotation Component 235, using one or more NLP techniques. As illustrated, Annotations 310 and 325 indicate the therapies mentioned or implicated by the statement. In one embodiment, these therapies are identified based on identifying the subject and object of the statement. Further, as illustrated, the Annotation 320 indicates the outcome (also referred to as the type) that is relevant to the statement. That is, in the illustrated embodiment, the Excerpt 305 discusses the relative efficacy of Drug A and Drug B, with respect to progression-free survival. Additionally, the Annotation 315 indicates the comparator (also referred to as qualifier or type qualifier), which indicates the comparison or statement being made (e.g., that the outcome, progression-free survival, was "superior."). Finally, as illustrated, the Annotation 330 corresponds to the cohort (or cohort qualifier) that the statement applies to.

In the illustrated embodiment, each of the relevant factors (e.g., Annotations 310, 315, 320, 325, and 330) are included within the same Excerpt 305. In embodiments, however, one or more of the relevant pieces of information can be located outside of the Excerpt 305. For example, in an embodiment, the cohort may be specified elsewhere in the document, and not explicitly given in the Excerpt 305. Similarly, one or more of the therapies or outcomes can be given elsewhere. For example, suppose the statement included "therapy Y led to the best results for the patients included in this study." In such an embodiment, the Extraction Component 230 and/or Annotation Component 235 can look elsewhere to determine the other therapy, the cohort, and the particular outcome type. Further, in an embodiment, the excerpt may only summarize one of the therapies in question and the Annotation Component 235 may look elsewhere to determine the complete definition of the therapy. For example, an excerpt may refer to "drug X-based therapy," where all of the components of this therapy are defined elsewhere in the document.

For example, the other therapies being tested may be listed in an introductory section, the cohort can be determined based on analyzing the patients involved, and the outcome of interest can be identified based on other sections of the document. In some embodiments, if the relevant information is not contained within the Excerpt 305, the confidence or weight of the comparative statement is reduced. In some embodiments, the Extraction Component 230 and/or Annotation Component 235 identify both the cohort (e.g., the patient population being studied) as well as cohort qualifiers (e.g., additional restrictions or limitations defining the group to whom the comparison is relevant). In one embodiments, the relevant cohort can identified based on other portions of the document (e.g., based on the abstract or study definitions). For example, a section of the document can indicate that the patients studied included females, aged 65-80, with hypertension. Additionally, the cohort qualifier ("high grade serious ovarian cancer") further restricts or limits the cohort to which the comparison is applicable.

As illustrated, the Cognitive Interpretation Component 105 (e.g., the Sentiment Component 240) then generates a RES 140A, based on the comparative statement. In the illustrated embodiment, as indicated by the arrow from Drug A to Drug B, the RES 140A indicates the relative efficacy of Drug A, as compared to Drug B. As illustrated, the sentiment is "positive," indicating that Drug A is better than Drug B with respect to the indicated cohort and the indicated outcome. Further, as illustrated, the outcome is "progression-free survival," and the cohort is individuals with "high grade serious ovarian cancer." As discussed above, in embodiments, this cohort can include additional attributes or definition, in combination with the cohort qualifiers found in the statement. Additionally, in the illustrated embodiment, the RES 140A includes a weight. In embodiments, this weight is based on a variety of factors, including the confidence of the NLP, the publication characteristics of the document, and the like.

Figure 3B:
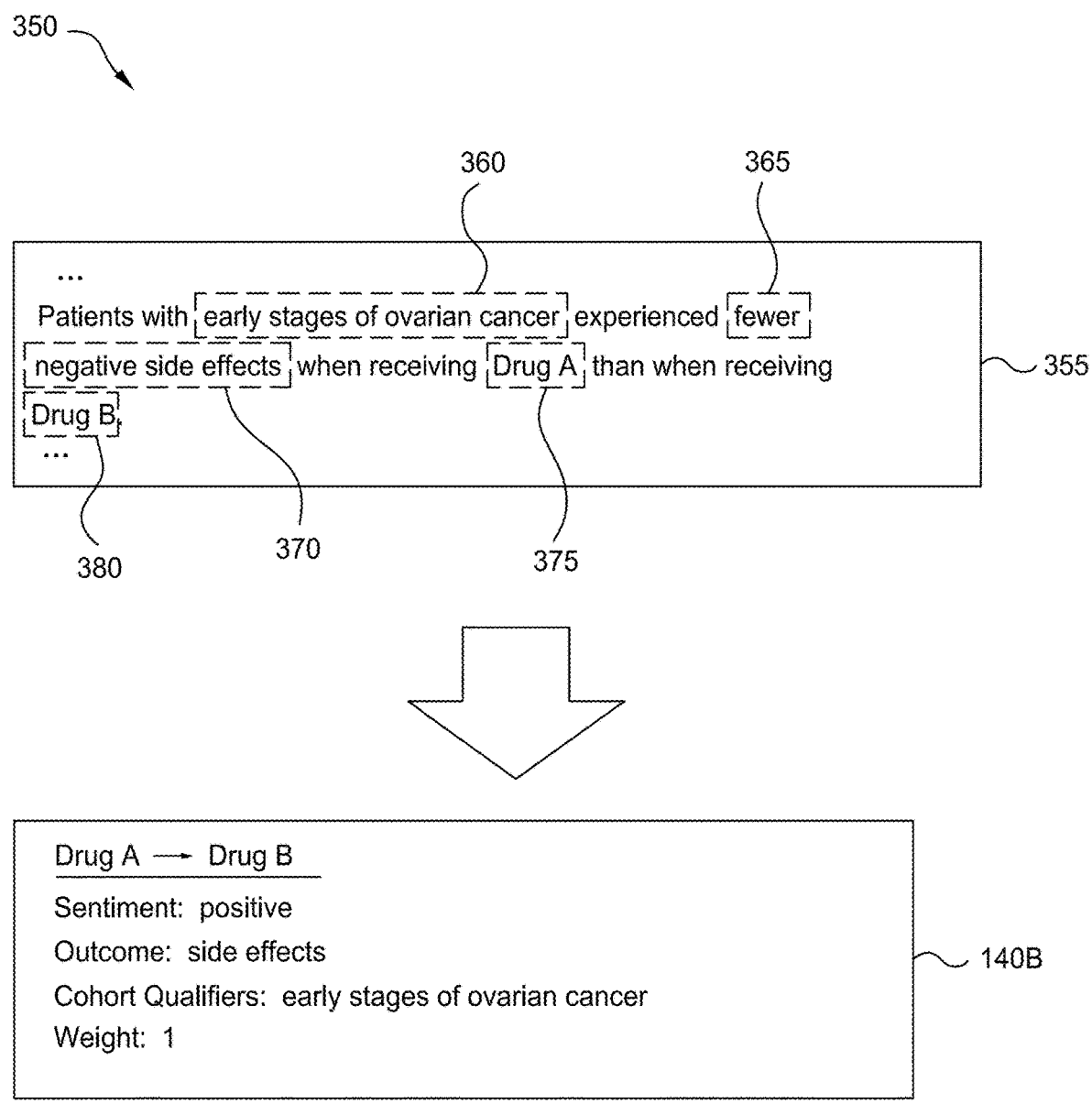
FIG. 3B illustrates a workflow for determining the efficacy for a therapy, as compared to a different therapy, according to one embodiment disclosed herein.

FIG. 3B illustrates a workflow 350 for determining the efficacy for a therapy, as compared to a different therapy, according to one embodiment disclosed herein. In the illustrated workflow 350, a comparative statement (included in an Excerpt 355) is annotated with Annotations 360, 365, 370, 375, and 380. As illustrated by the ellipses above and below the comparative statement, the original document can be any size or length. In an embodiment, the Excerpt 355 was extracted from a document (e.g., by the Extraction Component 230) based on determining that it included a comparative statement.

In an embodiment, the Excerpt 355 was annotated by the Annotation Component 235, using one or more NLP techniques. In the illustrated embodiment, Annotations 375 and 380 indicate the therapies mentioned or implicated by the statement. In one embodiment, these therapies are identified using the NLP models or techniques. Further, as illustrated, the Annotation 370 indicates the outcome of interest (also referred to as the type) that is relevant to the statement. That is, in the illustrated embodiment, the Excerpt 355 discusses the relative efficacy of Drug A and Drug B, with respect to negative side effects. Additionally, the Annotation 365 indicates the comparator (also referred to as qualifier or type qualifier), which indicates the comparison or statement being made (e.g., that the outcome, negative side effects, was "fewer."). Finally, as illustrated, the Annotation 360 corresponds to the cohort (or cohort qualifier) that the statement applies to.

As illustrated, the Cognitive Interpretation Component 105 (e.g., the Sentiment Component 240) then generates a RES 140B, based on the comparative statement. In the illustrated embodiment, as indicated by the arrow from Drug A to Drug B, the RES 140B indicates the relative efficacy of Drug A, as compared to Drug B. As illustrated, the sentiment is "positive," indicating that Drug A is better than Drug B with respect to the indicated cohort and the indicated outcome. That is, because the outcome itself is negative, the Sentiment Component 240 determines that a "worse" result in terms of the number or magnitude of side effects is, in fact, a positive result. Further, as illustrated, the outcome is "toxicity," and the cohort is individuals with "early stages of ovarian cancer." Additionally, in the illustrated embodiment, the RES 140B includes a weight. In embodiments, this weight is based on a variety of factors, including the confidence of the NLP, the publication characteristics of the document, and the like.

Figure 4:
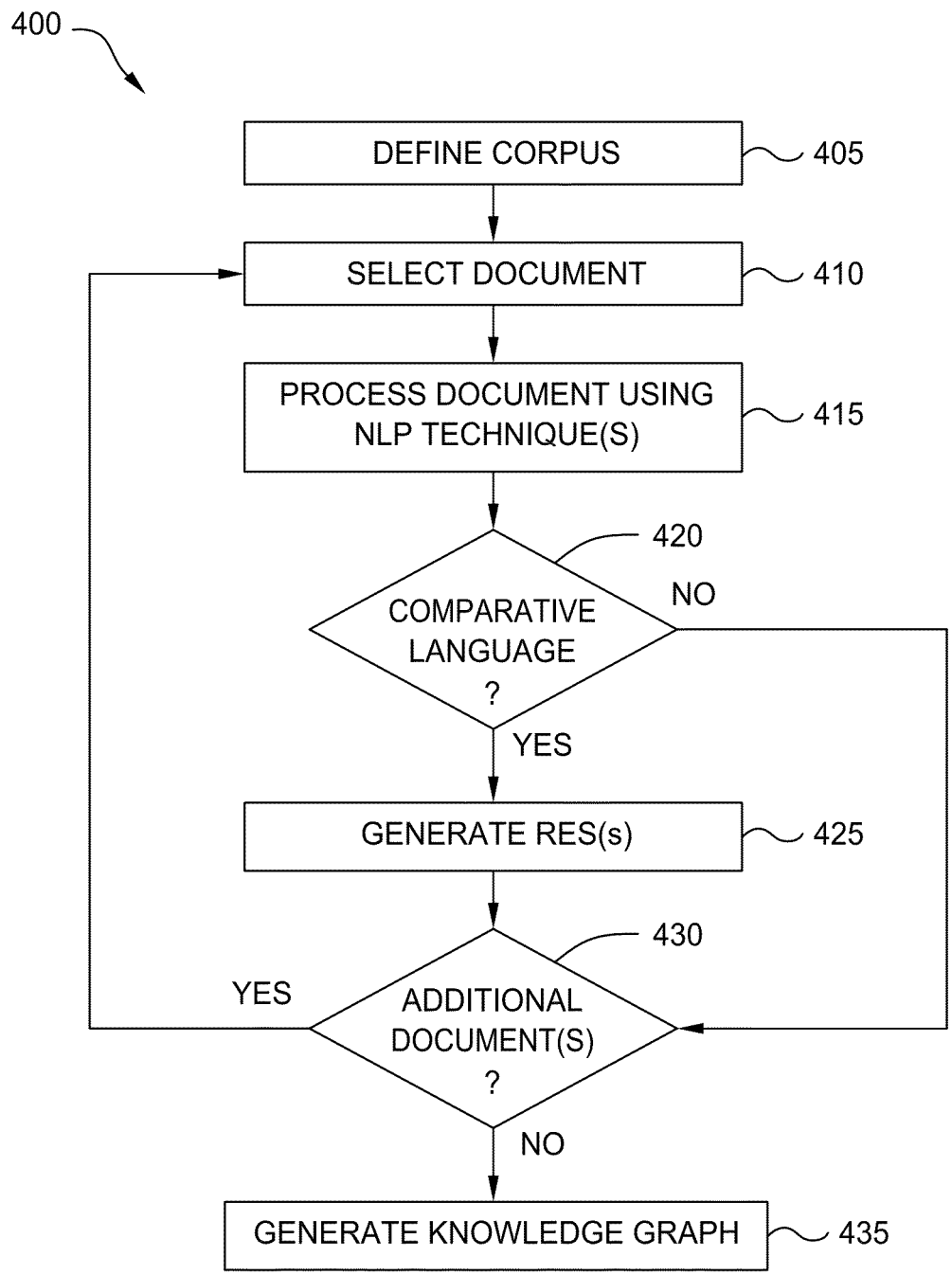
FIG. 4 illustrates a flow diagram illustrating a method for determining relative efficacies of various therapies, according to one embodiment disclosed herein.

FIG. 4 is a flow diagram illustrating a method 400 for determining relative efficacies of various therapies, according to one embodiment disclosed herein. The method 400 begins at block 405, where the Cognitive Interpretation Application 105 defines the relevant corpus. In one embodiment, this is based on a corpus indicated by the user or administrator. In some embodiments, the Cognitive Interpretation Application 105 receives one or more search terms, and builds the relevant corpus by searching or querying a larger corpus based on the search terms. In some embodiments, the Cognitive Interpretation Application 105 determines a set of documents in the identified corpus or subcorpus that have not yet been processed or ingested. For example, in one embodiment, a user can indicate a disorder or search term, and the Cognitive Interpretation Application 105 can first identify documents relating to the indicated terms, and then identify documents in the corpus that have not already been processed and ingested. In this way, the Cognitive Interpretation Application 105 can selectively analyze new documents in order to update and refine the knowledge base. Once the relevant corpus has been defined, the method 400 proceeds to block 410.

At block 410, the Cognitive Interpretation Application 105 selects a document from the corpus. At block 415, the Cognitive Interpretation Application 105 processes the all or a portion of the selected document using one or more NLP techniques. As discussed above, in some embodiments, the Cognitive Interpretation Application 105 analyzes specified portions of each document. In some embodiments, if no comparisons are found (or if one or more identified comparative statements are missing information or detail), the Cognitive Interpretation Application 105 can process additional sections or text. In one embodiment, the Cognitive Interpretation Application 105 also annotates the extracted excerpts during block 415. The method 400 then proceeds to block 420.

At block 420, the Cognitive Interpretation Application 105 determines whether the selected document (or the portion that was analyzed) includes any comparative statements. If so, the method 400 continues to block 425. If not, the method 400 proceeds to block 430. At block 425, the Cognitive Interpretation Application 105 generates one or more RESs 140 for each of the identified comparative statements found. The method 400 then continues to block 430. At block 430, the Cognitive Interpretation Application 105 determines whether there is at least one additional document in the corpus that is yet to be processed. If so, the method 400 returns to block 410. Otherwise, the method 400 continues to block 435, where the Knowledge Graph Component 110 generates (or updates) a knowledge graph.

Figure 5:
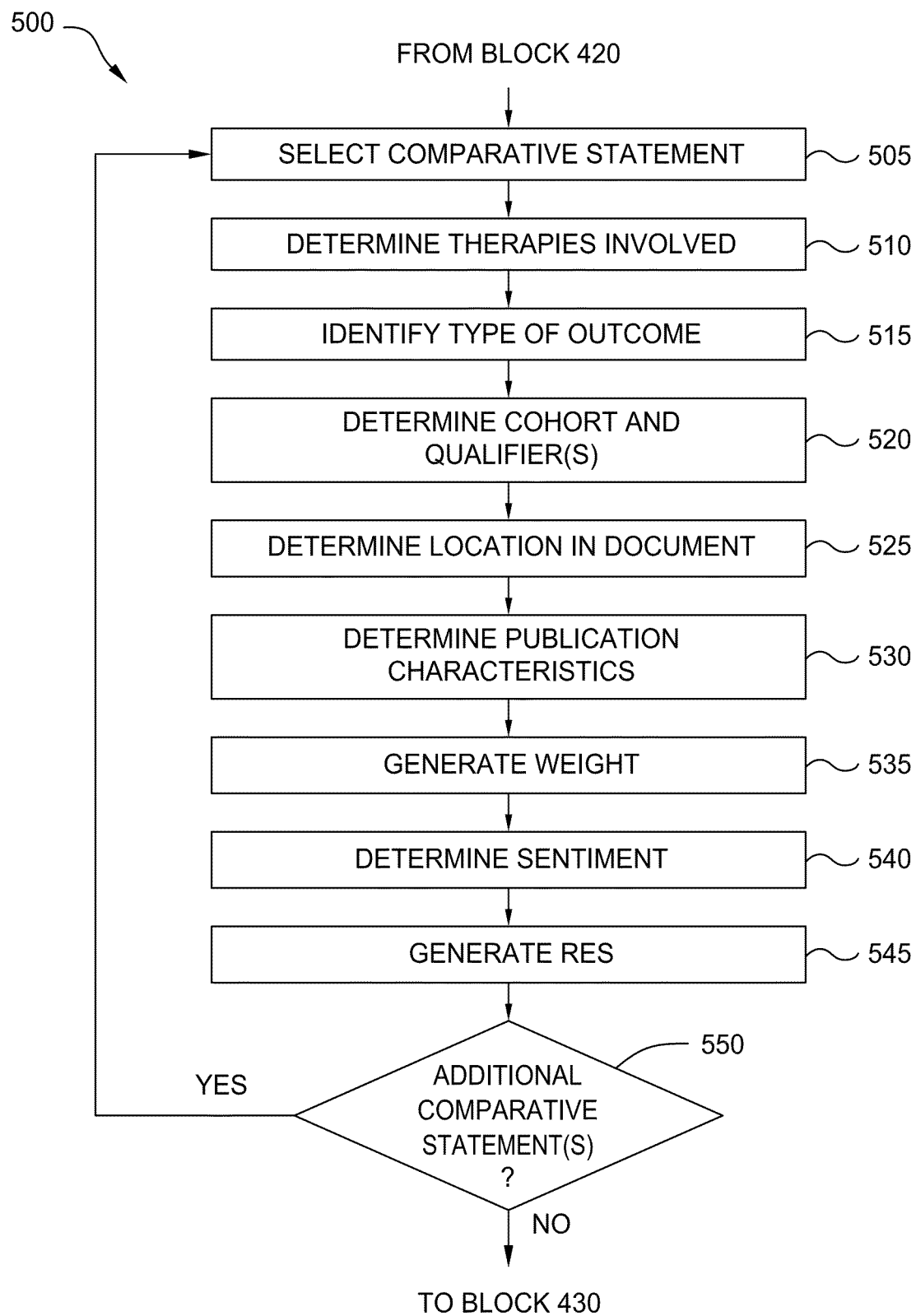
FIG. 5 is a flow diagram illustrating a method for generating relative efficacy structures summarizing comparisons between therapies, according to one embodiment disclosed herein.

FIG. 5 is a flow diagram illustrating a method 500 for generating RESs 140 summarizing comparisons between therapies, according to one embodiment disclosed herein. In one embodiment, the method 500 provides additional detail for block 425 in FIG. 4. The method 500 begins at block 505, where the Cognitive Interpretation Application 105 selects one of the comparative statements that were identified in the selected document. At block 510, the Cognitive Interpretation Application 105 identifies the therapies that are implicated by the selected statement. In one embodiment, the Cognitive Interpretation Application 105 utilizes NLP techniques to identify the relevant therapies. As discussed above, in some embodiments, the Cognitive Interpretation Application 105 parses other sections of the document, and/or other documents and data, in order to disambiguate any unknown or uncertain terms (e.g., ambiguous phrases or acronyms). The method 500 then continues to block 515.

At block 515, the Cognitive Interpretation Application 105 identifies the type of outcome the statement is addressing. That is, the Cognitive Interpretation Application 105 determines the particular outcome or effect that the selected statement is referring to. For example, in a medical embodiment, the outcomes can include overall survival, progression-free survival, remission, cure, death, complications, side effects, and the like. The method 500 then continues to block 520, where the Cognitive Interpretation Application 105 determines the cohort and/or cohort qualifiers that are relevant to the statement. For example, the cohort may be determined based on the patients being studied (e.g., as indicated by criteria used by the study authors when enrolling patients), and the cohort qualifiers can include any additional limitations included in the statement (e.g., "only patients above 65 saw a significant improvement.").

At block 525, the Cognitive Interpretation Application 105 determines the location in the selected document where the selected comparative statement was found. In one embodiment, block 525 comprises determining the section that the statement was in. In an embodiment, the sections are identified based on defined headings, metadata tags, and the like. In some embodiments, the weight of the generated RES 140 is adjusted based on the location. That is, in one embodiment, each section is associated with a respective weight or scale. For example, in one embodiment, the conclusion and abstract sections may be afforded higher weight than the general discussion section.

The method 500 then continues to block 530, where the Cognitive Interpretation Application 105 determines publication characteristics of the selected document that the statement was found in. For example, in one embodiment, the publication characteristics include a date when the document was published, the identity of the publisher, whether it has been peer-reviewed, and the like. In some embodiments, the publication characteristics also include the location in the document where the comparative statement was found. At block 535, the Cognitive Interpretation Application 105 generates a weight for the RES 140 based on the publication characteristics, and/or the determined location. In some embodiments, the Cognitive Interpretation Application 105 also considers any confidence values generated by the NLP models when parsing the text. Further, in one embodiment, the weight is based in part on the strength of the comparator used (e.g., whether the treatment is "slightly better" or "far superior").

The method 500 then continues to block 540, where the Cognitive Interpretation Application 105 determines the sentiment of the statement. In an embodiment, as discussed above, the Cognitive Interpretation Application 105 utilizes NLP to classify the statement as positive, negative, or neutral. Finally, at block 545, the Cognitive Interpretation Application 105 generates a RES 140 for the selected comparative statement based on the determined attributes, sentiment, and weight. At block 550, the Cognitive Interpretation Application 105 determines whether there is at least one additional comparative statement found in the document. If so, the method 500 returns to block 505. Otherwise, the method 500 terminates.

Figure 6:
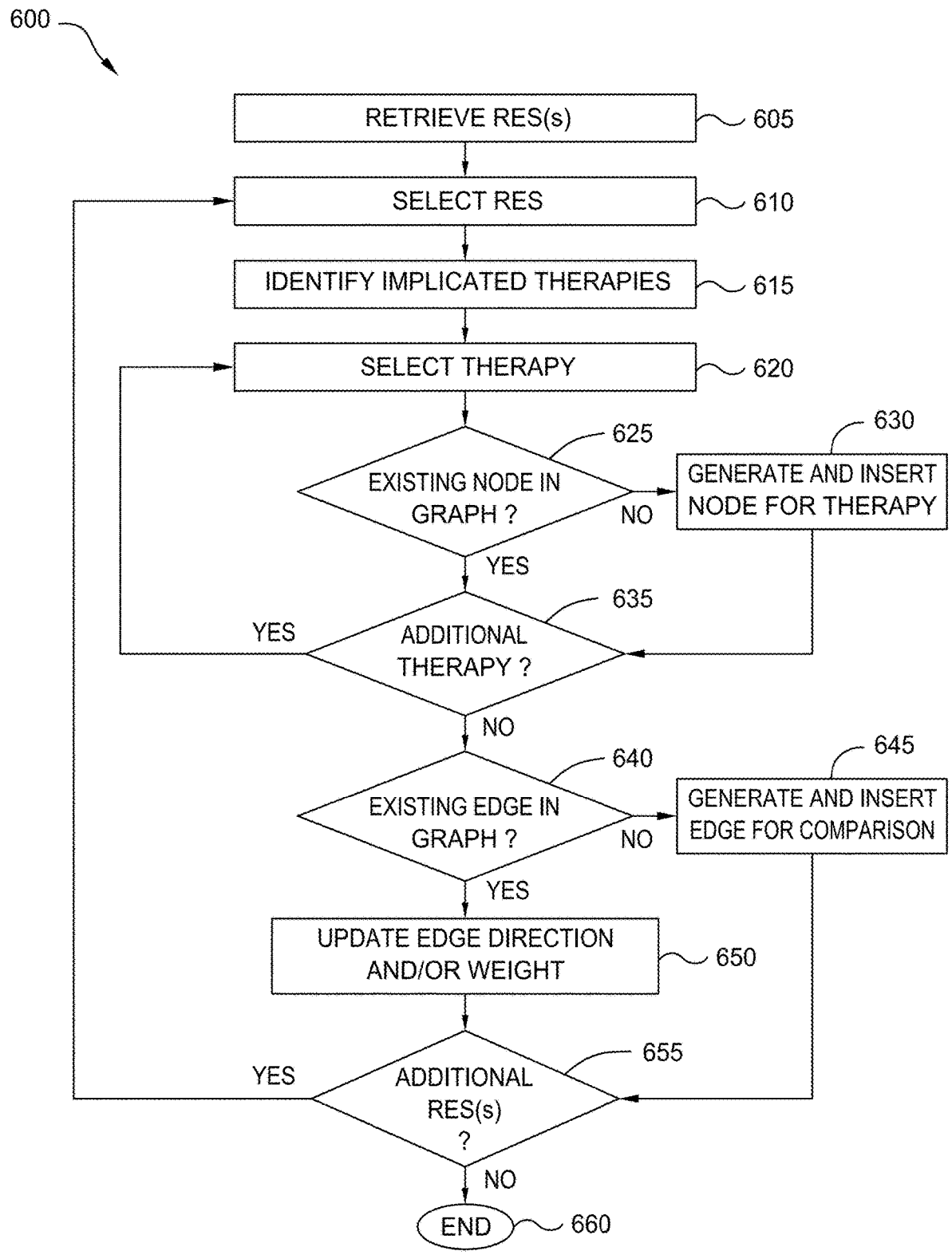
FIG. 6 is a flow diagram illustrating a method for generating a knowledge graph based on generated relative efficacy structures, according to one embodiment disclosed herein.

FIG. 6 is a flow diagram illustrating a method 600 for generating a knowledge graph based on generated relative efficacy structures, according to one embodiment disclosed herein. The method 600 begins at block 605, where the Knowledge Graph Component 110 retrieves one or more RES(s) 140 that were generated by the Cognitive Interpretation Application 105. At block 610, the Knowledge Graph Component 110 selects one of the RESs 140. The method 600 then proceeds to block 615, where the Knowledge Graph Component 110 identifies the therapies that are indicated by the selected RES 140. That is, the Knowledge Graph Component 110 determines which therapies are compared in the RES 140. At block 620, the Knowledge Graph Component 110 selects one of these identified therapies.

The method 600 continues to block 625, where the Knowledge Graph Component 110 determines whether there is an existing node in the knowledge graph for the selected therapy. As discussed above, in an embodiment, each node in the knowledge graph corresponds to a therapy. In some embodiments, a therapy can include a combination of treatments or mediations (e.g., a drug as well as physical therapy). If the selected therapy is already represented in the knowledge graph, the method 600 continues to block 635. If the selected therapy is not yet in the knowledge graph, the method 600 proceeds to block 630, where the Knowledge Graph Component 110 generates and inserts a new node into the graph to represent the selected therapy. The method 600 then continues to block 635.

At block 635, the Knowledge Graph Component 110 determines whether there are additional therapies in the selected RES 140. If so, the method 600 returns to block 620. Otherwise, the method 600 continues to block 640. In the illustrated embodiment, the Knowledge Graph Component 110 analyzes each therapy, and generates new nodes for each. In some embodiments, the knowledge graph is already constructed using a known or defined set of therapies. In such an embodiment, the Knowledge Graph Component 110 does not generate and insert new nodes. In some embodiments, in addition to an existing set of therapies, the Knowledge Graph Component 110 can further generate and insert nodes representing new therapies or new combinations of treatments that are identified in the RES 140.

In one embodiment, each node in the knowledge graph can be connected to zero or more other nodes, based on whether a comparison has been identified between the corresponding therapies. For example, in one embodiment, if two therapies have not been directly compared in the published literature, there will be no link or connection between the corresponding nodes. If, however, the therapies have been compared at least once, there will be an edge or connection between them. In some embodiments, each edge includes a number of dimensions indicating the directionality, the cohort(s) the edge applies to, the outcome(s) the edge applies to, and the like. For example, in such an embodiment, an edge may indicate that treatment A is better than treatment B, with respect to overall survival, in patients over 65. For patients under 65, however, there may be no edge or connection (if the therapies have not been compared for patients under 65), or there may be a link indicating that treatment B is better than treatment A. Similarly, with respect to a different outcome (such as progression-free survival or side effects), there may be no link, or a different link or connection may indicate that treatment B is better than treatment A. In some embodiments, the knowledge graph is constructed with a single edge connecting each pair of therapies, where that edge identifies all documents and/or RESs 140 that included a statement comparing the respective therapies. In another embodiment, the graph can include a respective edge to represent each respective RES 140 that is relevant to the respective pair of therapies.

In some embodiments, each edge in the graph is associated with a respective weight. This weight can be based on a variety of factors, including the number of times the relationship has been identified (e.g., the number of RESs 140 associated with the particular edge), the confidence or weight of each of those RESs 140, and the like. In some embodiments, as additional RESs 140 indicate the same relative efficacy (e.g., that one therapy is better than the other), the weight or strength of the edge is progressively strengthened. If, however, a RES 140 indicates the opposite comparison (e.g., that the first therapy is worse than the other), the weight or strength of the edge is reduced. In this way, each connection in the graph indicates an overall relative efficacy of the therapies, along with an associated strength or confidence in the accuracy of the comparison.

At block 640, the Knowledge Graph Component 110 determines whether there is an existing edge in the knowledge graph representing the relationship indicated by the selected RES 140. That is, in an embodiment, the Knowledge Graph Component 110 determines whether there is any link or connection between the identified therapies, with respect to the indicated cohort and outcome, regardless of the directionality of the relationship (e.g., regardless of whether the existing link matches the determined relative efficacy in the RES 140). In an embodiment, there may be any number of connections between the identified therapies with respect to other cohorts or other outcomes. The determination at block 640, however, is specific to the particular cohort and outcome specified in the RES 140.

In some embodiments, a particular RES 140 can include multiple comparisons. For example, if a statement included that treatment A was superior than all known treatments, the Cognitive Interpretation Application 105 can parse or analyze existing literature (or one or more knowledge graphs) to identify known treatments with respect to the disorder, cohort, and outcome. In such an embodiment, the RES 140 can include an indication of each of these known treatments. In other embodiments, a separate RES 140 is created for each of the comparisons (e.g., for each of the known treatments). In an embodiment, if the RES 140 includes comparisons to multiple therapies, the process discussed below (and reflected by blocks 640, 645, and 650) is repeated for each.

If the Knowledge Graph Component 110 determines, at block 640, that there is no edge in the graph representing the comparison, with respect to the identified cohort and outcome, the method 600 continues to block 645, where the Knowledge Graph Component 110 generates and inserts one. In one embodiment, the directionality of the new edge is based on the sentiment reflected in the selected RES 140 (e.g., positive, negative, or neutral). Further, in an embodiment, the initial weight or strength of the new edge is based on the weight or confidence of the RES 140. In this way, the knowledge graph is updated to reflect that the published literature includes a direct comparison between the therapies, and indicates the relative efficacy of the therapies (e.g., based on the directionality of the edge).

If the Knowledge Graph Component 110 determines, at block 640, that an edge already exists for the indicated comparison, with respect to the specified cohort and outcome, the method 600 continues to block 650, where the Knowledge Graph Component 110 updates the weight and/or direction of the identified edge. In some embodiments, the Knowledge Graph Component 110 instead inserts a new edge, depending on the particular design that will be used to represent multiple comparisons between two treatments in the knowledge graph. As discussed above, in one embodiment, this updating includes adjusting the weight of the edge based on the weight and directionality of the selected RES 140. In an embodiment, if the sentiment reflected by the RES 140 is in the same direction as the existing edge (e.g., the RES 140 and the edge agree that one treatment is superior), the weight or strength is increased. If the directions are opposite, the weight is decreased. Similarly, in one embodiment, if the selected RES 140 has a neutral sentiment (indicating that the therapies are equally effective), the weight of the edge is reduced, regardless of which direction it currently points. If the edge is already neutral, a neutral weight or strength can be increased, indicating that there is additional evidence that the therapies are equally effective.

In one embodiment, the amount that the edge strength is changed is dependent on the magnitude of the confidence or weight associated with the RES 140. If the RES 140 is associated with a high weight, the strength of the edge will be adjusted a greater amount than if the weight of the RES 140 was low. In one embodiment, if the weight falls below a predefined threshold (e.g., within a defined distance from zero), the edge is removed from the graph, indicating that there is no medical consensus regarding the relationship or relative efficacy. In other embodiments, the edge is updated to have no direction, reflecting that there is no solid consensus, and results are mixed (e.g., indicating that the comparison has been studied, but that there is no strong evidence supporting either therapy as more effective than the other). In some embodiments, this edge is retained with a low weight or strength, and is assigned a neutral sentiment to indicate that neither therapy is clearly superior to the other.

Similarly, in some embodiments, if an edge is neutral (or close to neutral) and the weight adjustment would cause the weight to be negative, the direction of the edge is switched, indicating a (potentially weak) new consensus that the relative efficacy of the treatments is reversed from the previously-understood comparison. In some embodiments, each edge in the graph is associated with a directionality as well as a weight or strength of the edge (representing the strength of the evidence). The method 600 then proceeds to block 655, where the Knowledge Graph Component 110 determines whether there is at least one additional RES 140 that has not been analyzed and ingested into the knowledge graph. If so, the method 600 returns to block 610 to select a next RES 140. Otherwise, the method 600 terminates at block 660. In this way, the Knowledge Graph Component 110 can update and refine the knowledge graph based on new therapies and studies. In embodiments, the knowledge graph is a multi-dimensional representation of the medical consensus as to relative efficacies of any number of therapies, with respect to any combination of particular cohorts and outcomes. Advantageously, embodiments of the present disclosure enable the graph to be continuously and rapidly updated when new published literature becomes available, such that the knowledge graph represents the most up-to-date and accurate representation possible. Further, because of the high-dimensionality of the graph (e.g., because the relative efficacies differ based on the individual cohort and outcome), the knowledge graph provides additional data that is far more granular, and is not otherwise available to healthcare providers.

In some embodiments, the knowledge graph can be accessed and searched by healthcare providers in order to determine optimal treatments for a particular patient. For example, in an embodiment, the provider can search the knowledge graph (e.g., using the User Interface 280 of the Client Device 255) to identify therapies and/or relative efficacies that are relevant to the cohort to which the patient belongs. That is, in an embodiment, the knowledge graph can be parsed to identify comparisons that are relevant to a patient in a particular cohort (e.g., having a particular set of attributes). In some embodiments, the provider can also filter, sort, or search the knowledge graph based on the desired outcome. In one embodiment, based on these relative efficacies, the therapies can be scored and ranked, in order to identify the most optimal therapy. This allows the provider to make improved decisions with respect to treating the patient.

In some embodiments, the outcomes types are associated with a predefined hierarchy. That is, some outcomes (e.g., progression-free survival) may be considered more important than other outcomes (e.g., side effects), and therefore be weighted more heavily when aggregating the relative efficacies with respect to each outcome in order to determine an overall relative efficacy (e.g., an overall optimal or best therapy, with respect to all outcomes). In such an embodiment, the ranking or scoring of the therapies may take into account the relative efficacies, as well as the importance or weight of the particular outcome. That is, although a first therapy may be the best with respect to side effects, it may be given a lower score than a second therapy that is better with respect to survival.

Although not illustrated, in some embodiments, the Knowledge Graph Component 110 can further generate nodes for which there are no existing comparisons. For example, if a paper or article includes a study of a particular therapy, but does not include any comparison to other therapies, the Knowledge Graph Component 110 can generate a node for the therapy, without necessarily connecting the node to any other therapies. Further, in some embodiments, the Knowledge Graph Component 110 includes an indication as to the efficacy of each therapy. For example, in such an embodiment, the Cognitive Interpretation Application 105 can determine the overall efficacy for each particular therapy, in addition to determining the relative efficacies of therapies, as compared to each other. This information can then be included in the corresponding node in the knowledge graph. In embodiments, the efficacy can include a percentage of patients who the therapy helped, and/or an amount that the therapy helped.

Figure 7:
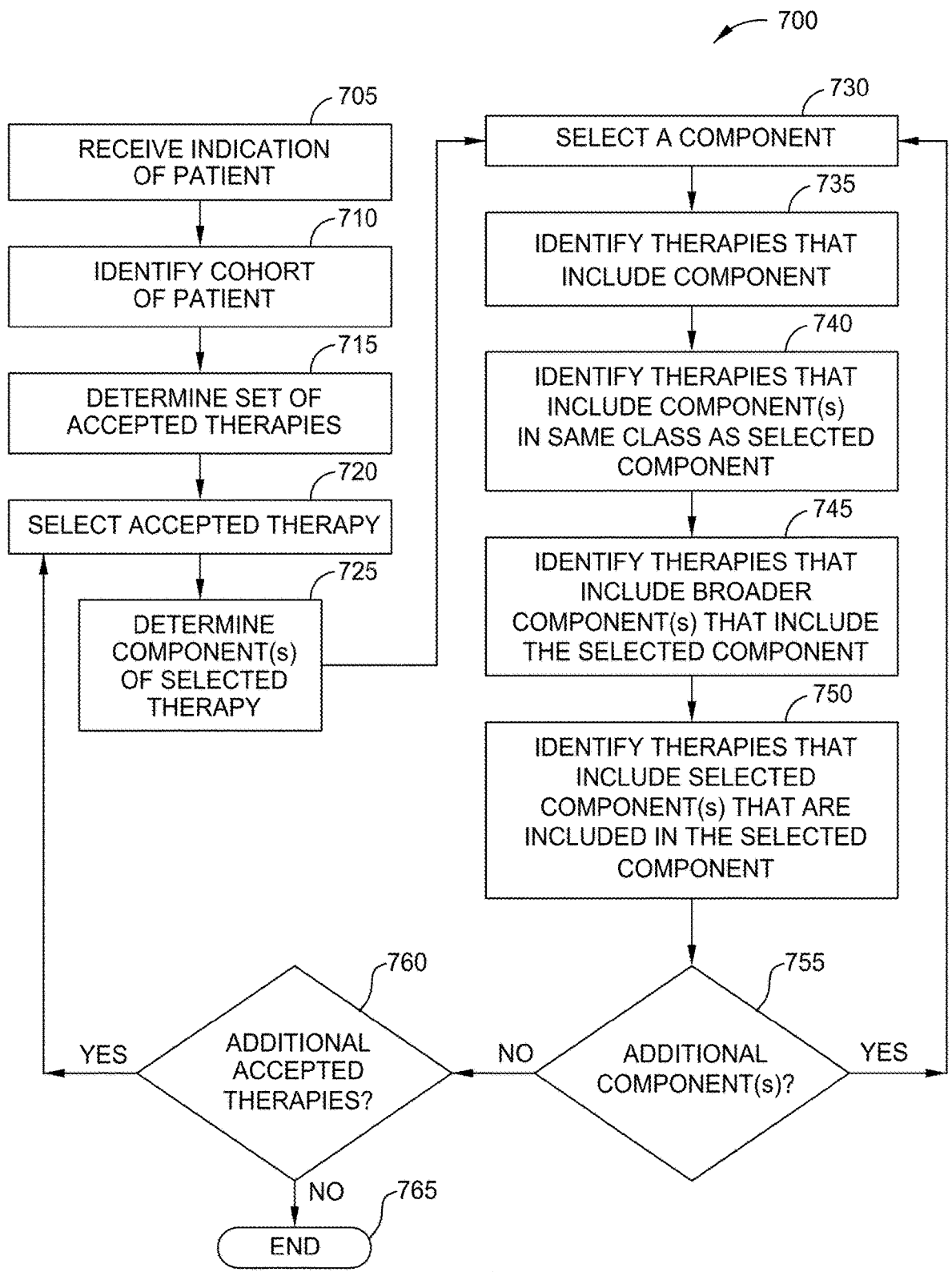
FIG. 7 is a flow diagram illustrating a method for identifying potential therapies beyond a bounded set of therapies, according to one embodiment disclosed herein.

FIG. 7 is a flow diagram illustrating a method 700 for identifying potential therapies beyond a bounded set of therapies, according to one embodiment disclosed herein. The method 700 begins at block 705, where the Therapy Suggestion Application 165 receives an indication of a patient to be treated. As discussed above, in some embodiments, the Therapy Suggestion Application 165 receives a patient profile for the patient, where the patient profile includes one or more attributes of the patient. In some embodiments, the Therapy Suggestion Application 165 can additionally or alternatively identify attributes specified by a user, or found in one or more EMRs. Additionally, in some embodiments, as discussed above, the Therapy Suggestion Application 165 can receive an indication of the cohort(s) to be evaluated.

At block 710, if the cohort was not specified, the Therapy Suggestion Application 165 identifies the cohort of the patient, based on the attributes provided or discovered. In some embodiments, when identifying and evaluating therapies for the patient, the Therapy Suggestion Application 165 only considers data that would apply to the patient. For example, in one embodiment, the Therapy Suggestion Application 165 only considers data (e.g., comparisons and efficacy statements) that is associated with or corresponds to the patient's cohort or attributes. In one embodiment, if the comparison is identified in a clinical trial or study, the Therapy Suggestion Application 165 verifies that the patient would have qualified to be a participant in the trial (based on the cohort and/or attributes), prior to utilizing the data. In some embodiments, this information is contained within the knowledge graph.

The method 700 then proceeds to block 715, where the Therapy Suggestion Application 165 determines the set of accepted therapies for the cohort. As discussed above, in one embodiment, this comprises retrieving a predefined set of treatments that are accepted or specified by a standards-setting institution. In some embodiments, determining the set of accepted therapies includes identifying therapies that have been historically used by the user, or at an institution associated with the user (e.g., at the hospital or clinic where the user works). At bock 720, the Therapy Suggestion Application 165 selects one of these accepted therapies, and at block 725, the Therapy Suggestion Application 165 determines the therapy component(s) included in the selected therapy. As discussed above, in one embodiment, each therapy can include one or more components, including medications, procedures (e.g., surgery or other operations), instructions, activities to partake in or refrain from, and the like.

At block 730, the Therapy Suggestion Application 165 selects a component from the determined set of components for the selected accepted therapy. The method 700 then proceeds to block 735, where the Therapy Suggestion Application 165 identifies therapies in the knowledge graph that include the selected component. In one embodiment, as discussed above, the Therapy Suggestion Application 165 considers only those therapies that are associated with the cohort of the patient, as discussed above. In an embodiment, the therapy is associated with the cohort if the knowledge graph includes an indication to that effect. In one embodiment, the therapy is associated with the cohort if it has been tested or used in treating the cohort, or patients who share one or more attributes of the patient. In one embodiment, the Therapy Suggestion Application 165 searches or queries the knowledge graph based on the cohort and/or disorder to identify therapies that are associated with the cohort, and analyzes each to determine the therapy components included.

The method 700 then continues to block 740, where the Therapy Suggestion Application 165 identifies therapies that have one or more components in the same class as the selected component. In one embodiment, two components (e.g., two medications or drugs) are considered by the Therapy Suggestion Application 165 to be in the same class if they have similar chemical structures or utilize the same mechanism of action or a related mode of action. In one embodiment, the medications are considered to be in the same class if they are used to treat the same disease or condition. In an embodiment, the classes are defined in medical literature, and/or in a knowledge graph showing relationships between therapy components. The method 700 then proceeds to block 745.

At block 745, the Therapy Suggestion Application 165 identifies therapies that include one or more components that are broader than the selected component. For example, if the selected component is a particular type of antihistamine, the Therapy Suggestion Application 165 can identify other therapies that include a generic "antihistamine" component. Further, at block 750, the Therapy Suggestion Application 165 identifies therapies that include more specific components that are included within the selected component. For example, if the selected component is "cognitive therapy," the Therapy Suggestion Application 165 can identify therapies that mention specific types of cognitive therapy. The method 700 then continues to block 755.

At block 755, the Therapy Suggestion Application 165 determines whether there is at least one additional component in the determined set of components included in the selected accepted therapy. If so, the method 700 returns to block 730. If not, the method 700 proceeds to block 760, where the Therapy Suggestion Application 165 determines whether there is at least one additional accepted therapy to be evaluated. If so, the method 700 returns to block 720. Otherwise, the method 700 terminates at block 765.

In one embodiment, when identifying potential treatments, the Therapy Suggestion Application 165 excludes any therapies that are included in the accepted set. That is, when a potential therapy is found, the Therapy Suggestion Application 165 can exclude or ignore it if it is already included in the bounded set of accepted treatments. In this way, the Therapy Suggestion Application 165 identifies an unbounded set of treatments that are related or similar to the accepted treatments (because they have at least one similar or identical component). In some embodiments, the Therapy Suggestion Application 165 only considers therapies that have been used to treat the particular disorder, as well.

In one embodiment, the Therapy Suggestion Application 165 includes all therapies that have at least one component satisfying the criteria, discussed above. In some embodiments, however, the Therapy Suggestion Application 165 only includes therapies that have a threshold number of components satisfying the criteria. In a related embodiment, potential therapies are included only if a threshold percentage or ratio of their components satisfies one or more of the above-discussed criteria. In the illustrated embodiment, the Therapy Suggestion Application 165 does not consider the topology of the network graph when identifying the set of potential therapies. That is, the Therapy Suggestion Application 165 does not determine or consider whether the potential components are better or worse than the accepted set, or if they have even been compared to the accepted set. In some embodiments, the evaluation and analysis of the topology of the graph is discussed with reference to FIG. 8, below.

Figure 8:
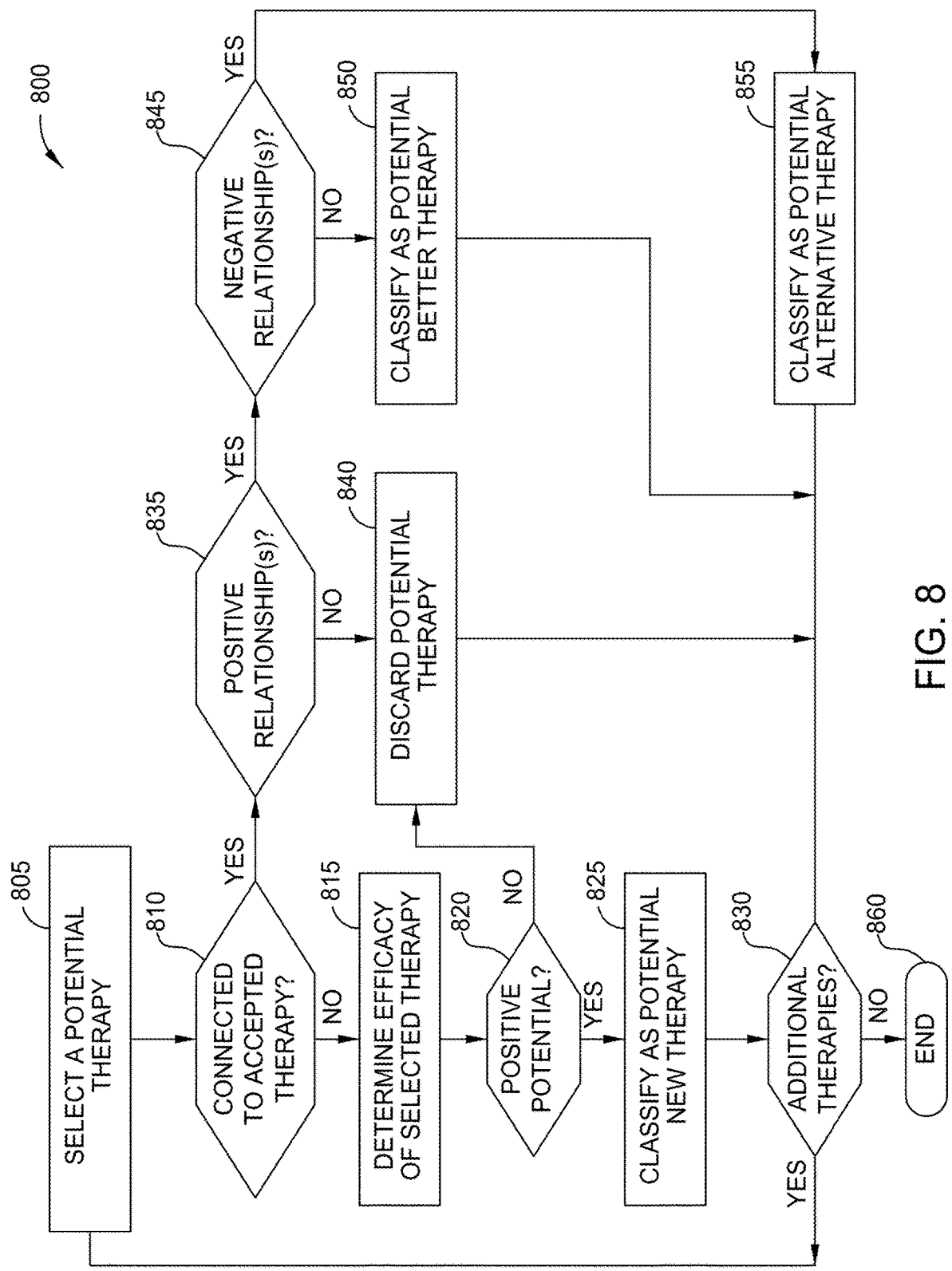
FIG. 8 is a flow diagram illustrating a method for classifying potential therapies in an unbounded set, according to one embodiment disclosed herein.

FIG. 8 is a flow diagram illustrating a method 800 for classifying potential therapies in an unbounded set, according to one embodiment disclosed herein. The method begins at block 805, where the Therapy Suggestion Application 165 selects a potential therapy. In one embodiment, the potential therapy is selected from the list or set of potential therapies generated using the method 700, as discussed above. The method 800 then continues to block 810, where the Therapy Suggestion Application 165 determines whether the selected therapy is connected to one or more accepted therapies in the knowledge graph. In an embodiment, the connection may be a direct connection (e.g., one or more edges connect directly from the selected potential therapy to one or more accepted therapies in the bounded set). As discussed above, in one embodiment, the presence of an edge in the graph indicates that the therapies represented by the corresponding end nodes have been directly compared in at least one document.

In some embodiments, determining whether the selected potential therapy is connected to any accepted therapies includes determining whether there is an indirect connection in the graph. For example, if there is an edge between the potential therapy and a first therapy (e.g., because the potential therapy was, at some point, compared to the first therapy), as well as a connection between the first therapy and the accepted therapy, the Therapy Suggestion Application 165 can determine that the potential therapy is indirectly connected to the accepted therapy. In one embodiment, the Therapy Suggestion Application 165 determines they are connected based on determining that the directionality of these connections allows the Therapy Suggestion Application 165 to make a relative efficacy conclusion. For example, if the knowledge graph indicates that therapies A and B are both better than C, the Therapy Suggestion Application 165 cannot conclude whether A is superior to B. Thus, in one embodiment, the Therapy Suggestion Application 165 may determine that they are disconnected.

In the illustrated embodiment, if the potential therapy is not connected to the accepted therapy, the method 800 proceeds to block 815, where the Therapy Suggestion Application 165 determines the efficacy or outcomes of the selected potential therapy. In an embodiment, this can include determining whether the therapy has an overall "positive" sentiment, as indicated by the corresponding node. For example, if the potential therapy was described as "promising" or "effective" in a non-comparative statement in one or more documents, the knowledge graph may indicate that the therapy is positive or good, overall. In some embodiments, the Therapy Suggestion Application 165 determines the outcomes reported for the therapy, the percentages or percentiles of patients achieving each outcome, and the like. In one embodiment, the Therapy Suggestion Application 165 identifies edges or connections that link to the node corresponding to the therapy (if any are present). The Therapy Suggestion Application 165 can then determine whether the therapy tends to be positive or negative (or neutral) with respect to other therapies, or whether one or more positive relationships exist.

The method 800 then proceeds to block 820, where the Therapy Suggestion Application 165 determines whether this determined efficacy indicates that the selected therapy has potential to be positive or effective. If not, the method 800 continues to block 840, where the Therapy Suggestion Application 165 discards the potential therapy and removes it from the set of potential therapies to be considered. In some embodiments, the Therapy Suggestion Application 165 only discards the therapy upon determining that it has a negative outlook, as opposed to neutral. Further, in some embodiments, the Therapy Suggestion Application 165 retains the therapy, but classifies it as an unlikely potential therapy or a questionable potential therapy. In some embodiments, when generating scores for each potential therapy, questionable therapies are given a low weight, such that they are unlikely to appear near the top of the results. The method 800 then proceeds to block 830.

If, however, the Therapy Suggestion Application 165 determines at block 820 that the potential therapy has positive or promising potential, the method 800 proceeds to block 825, where the Therapy Suggestion Application 165 classifies the potential therapy as a potential new therapy. In one embodiment, each classification of potential therapy is associated with a distinct weight, which affects the score or confidence of the potential therapy when identifying optimal treatment options. In some embodiments, these weights are defined by a user (e.g., based on whether the user is most interested in finding and evaluating new therapies, alternative therapies, or better therapies). In one embodiment, the questionable or improbable therapies are given the lowest weight, relative to the other classifications. The method 800 then proceeds to block 830, where the Therapy Suggestion Application 165 determines whether there is at least one additional potential therapy to be analyzed. If so, the method 800 returns to block 805. If not, the method 800 terminates.

Returning to block 810, if the Therapy Suggestion Application 165 determines that the selected potential therapy is connected (directly or indirectly) to at least one of the accepted therapies (e.g., such that the Therapy Suggestion Application 165 can determine a relative efficacy of the potential therapy, with respect to the accepted therapy), the method 800 proceeds to block 835. At block 835, the Therapy Suggestion Application 165 determines whether one or more of the identified connections between the potential therapy and the accepted therapies are positive. That is, the Therapy Suggestion Application 165 determines whether the potential therapy has a positive relative efficacy, indicating that it is (or may be) superior to the accepted therapy. As discussed above, in embodiments, this positive relationship indicates that at least some evidence exists to support the assertion that the potential therapy is superior to at least one of the accepted therapies, with respect to the cohort and/or disorder.

If the Therapy Suggestion Application 165 determines that none of the connections are positive, the method 800 proceeds to block 840, where the potential therapy is discarded. That is, because there is no evidence (or no evidence that has been ingested into the knowledge graph) indicating that the potential therapy is superior to the accepted therapies, the Therapy Suggestion Application 165 ignores the potential therapy and removes it from the list of consideration. As discussed above, in some embodiments, the Therapy Suggestion Application 165 assigns the potential therapy to the list of questionable or improbable therapies, such that it is analyzed with a low weight or confidence, in order to reflect that no evidence exists to indicate it is superior to any accepted therapies. The method 800 then proceeds to block 830.

Returning to block 835, if the Therapy Suggestion Application 165 determines that at least one connection is positive (e.g., indicating that there is at least some evidence indicating that the potential therapy is superior to at least one of the accepted therapies), the method 800 proceeds to block 845. At block 845, the Therapy Suggestion Application 165 determines whether there are any negative connections or relationships linking the selected potential therapy to any of the accepted therapies. That is, the Therapy Suggestion Application 165 determines whether there is any evidence represented in the knowledge graph that indicates that the selected potential therapy is inferior to at least one accepted therapy. If so, the method 800 proceeds to block 855, where the Therapy Suggestion Application 165 classifies the potential therapy as a potential alternative therapy. Thus, in the illustrated embodiment, the Therapy Suggestion Application 165 identifies the potential therapy as having potential to be an alternative therapy to the accepted therapies, based on determining that there is evidence that it is superior to one or more accepted therapies, but inferior to one or more other accepted therapies. The method 800 then continues to block 830.

Returning to block 845, if the Therapy Suggestion Application 165 determines that there are no negative connections or relationships between the potential therapy and the accepted therapies, the method 800 proceeds to block 850.

At block 850, the Therapy Suggestion Application 165 classifies the therapy as a potential better or superior therapy. That is, because the knowledge graph includes evidence that the potential therapy is better than at least one accepted therapy, and there is no evidence that the potential therapy is inferior to any accepted therapy, the Therapy Suggestion Application 165 indicates that it is potentially a superior or better therapy that should be considered when treating patients in the cohort. The method 800 then proceeds to block 830.

Figure 9:
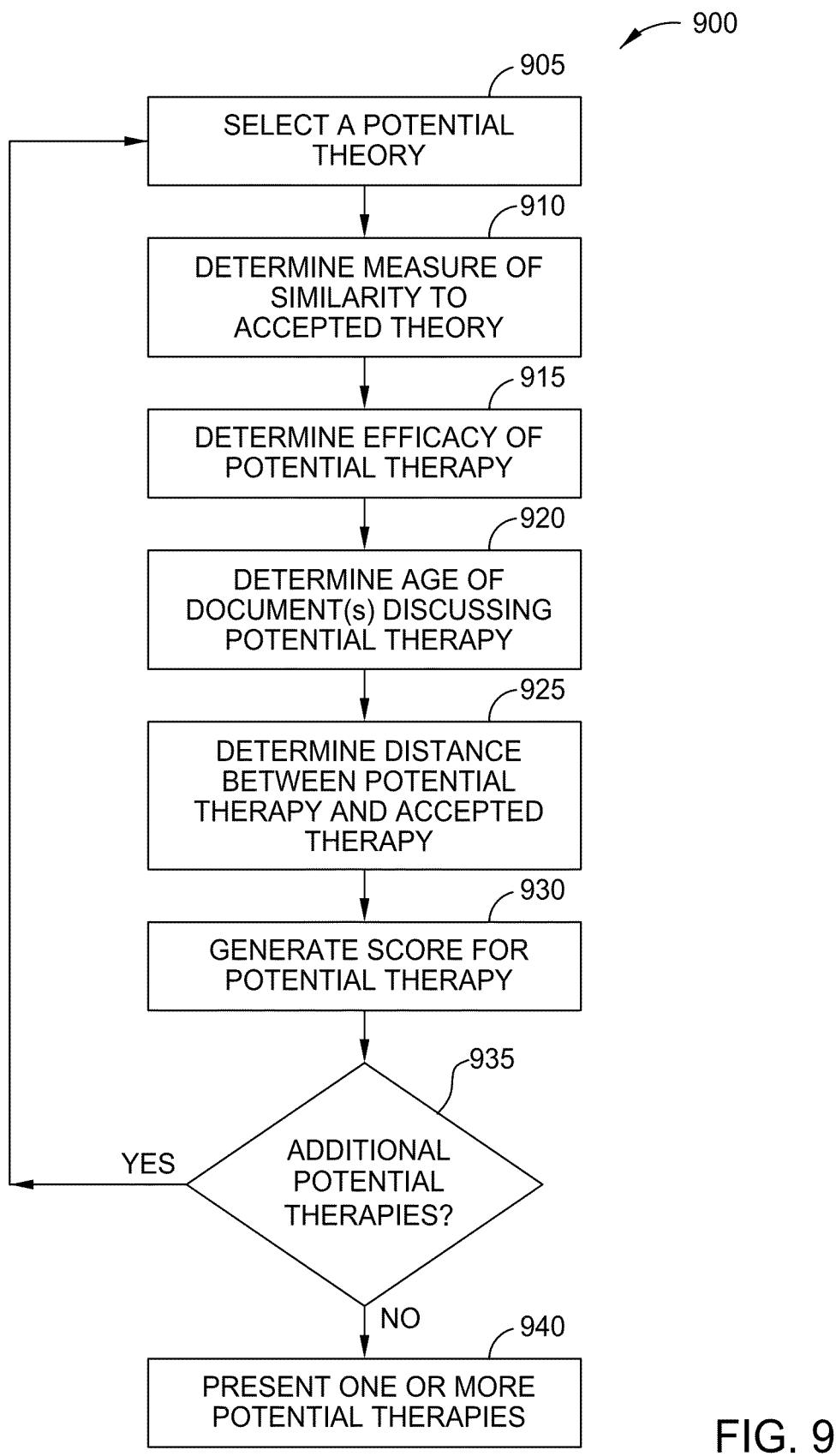
FIG. 9 is a flow diagram illustrating a method for evaluating unbounded potential therapies, according to one embodiment disclosed herein.

FIG. 9 is a flow diagram illustrating a method 900 for evaluating unbounded potential therapies, according to one embodiment disclosed herein. The method 900 begins at block 905, where the Therapy Suggestion Application 165 selects a potential therapy from the determined set of potential therapies, as discussed above. At block 910, the Therapy Suggestion Application 165 determines a measure of similarity between the selected potential therapy and one or more accepted therapies from the bounded set. In one embodiment, the Therapy Suggestion Application 165 generates a respective similarity measure between the potential therapy and each respective accepted therapy. In some embodiments, the similarity score for the potential therapy corresponds to the highest similarity among the accepted therapies. In one embodiment, the similarity measure for the potential therapy is determined by aggregating the individual measures, such as by summing or averaging them.

In one embodiment, each measure of similarity is determined based on a variety factors, including the number of components in the potential therapy that match or correspond to components in an accepted therapy. In some embodiments, this correspondence includes not only identical matches, but also components that are in the same class, or are a more generic or specific type. In one embodiment, each type of match or correspondence is associated with a distinct weight. For example, identically matching components can be given a highest weight. In an embodiment, components that are more specific in the potential therapy are given a next highest weight, followed by components that are in the same class, and finally by components that are more general or broad in the potential therapy. In some embodiments, in addition to or instead of utilizing the overall number of matching components, the Therapy Suggestion Application 165 considers the ratio or percentage of components in the potential therapy that match the accepted therapy. In this way, the Therapy Suggestion Application 165 can generate the similarity measure based in part on how much of the potential therapy corresponds to or matches with the accepted therapies.

The method 900 then continues to block 915, where the Therapy Suggestion Application 165 determines the efficacy of the selected potential therapy, if available. In some embodiments, as discussed above, the knowledge graph indicates an efficacy of the potential therapy, or indicates how patients responded to the therapy (e.g., what percentage of patients experienced each potential outcome). The method 900 proceeds to block 920, where the Therapy Suggestion Application 165 determines the age of the node corresponding to the potential therapy, and/or the connection(s) between the potential therapy and the accepted set of therapies. That is, in an embodiment, the Therapy Suggestion Application 165 identifies one or more documents that were used to generate the node corresponding to the potential therapy, and/or the connection(s) between the potential therapy and the accepted set of therapies. As discussed above, in an embodiment, each node and connection in the knowledge graph is generated and refined based on evidence collected from published literature (e.g., comparative and non-comparative statements). In the illustrated embodiment, the Therapy Suggestion Application 165 identifies the documents that are related to the potential therapy, and determines an age of at least one.

In one embodiment, the Therapy Suggestion Application 165 determines the age of the first document associated with the potential therapy (e.g., the oldest document). In other embodiments, the Therapy Suggestion Application 165 utilizes the age of the newest document. In one embodiment, the Therapy Suggestion Application 165 determines the average or median age of the documents associated with the potential therapy. The method 900 then continues to block 925, where the Therapy Suggestion Application 165 determines the distance in the knowledge graph between the potential therapy and one or more accepted therapies. In an embodiment, the distance refers to the minimum number of edges or connections required to link the potential therapy to an accepted therapy. For example, if the potential therapy has been directly compared to an accepted therapy, the distance is one. Similarly, if the potential therapy has been compared to a second therapy, and the second therapy has been compared to an accepted therapy, the distance is two. In an embodiment, if the potential therapy is disconnected from the accepted therapies, the distance is undefined or infinite.

The method 900 then proceeds to block 930, where the Therapy Suggestion Application 165 generates a score for the selected potential therapy based on the measure of similarity, the efficacy, the age of the associated document(s), and the knowledge distance. In one embodiment, the similarity measure is directly related to the generated score, such that a higher similarity measure leads to a higher generated score. Similarly, in an embodiment, a better efficacy of the potential therapy is correlated with a higher score. In one embodiment, the age of the document(s) associated with the potential therapy is inversely related to the score, such that a younger age leads to a higher score. For example, in such an embodiment, the younger document(s) may yield higher scores because it indicates that the potential therapy may only be excluded by nature of being new, rather than because it has been considered and rejected. Further, in an embodiment, a closer distance between the potential therapy and the accepted therapies yields a higher score. In one embodiment, a therapy that is disconnected (e.g., that has infinite distance) is given a lower score as well.

In some embodiments, the score of the potential therapy is based further on the precision or relevancy of the individual documents. For example, in one embodiment, a precision or relevancy score is generated for each document, based on how closely the relevant cohort in the document matches the patient being treated. For example, in such an embodiment, if the patient matches the cohort, such that they could have participated in the study, the paper will be given a high weight. In contrast, if the patient matches only a subset of the attributes required by the paper, the document can nevertheless be considered, but with a reduced weight or confidence, based on determining that its precision is lower.

In some embodiments, the generated score is weighted based on the classification of the potential therapy. For example, as discussed above, in one embodiment, potential superior therapies are associated with a higher weight than potential alternative therapies, which are associated with a higher weight than potential new therapies, which are associated with a higher weight than improbable therapies. Of course, in some embodiments, these weights are adjusted based on preferences or settings provided by the user. Further, in some embodiments, the potential therapies are intermingled such that a potential alternative therapy may score higher than a potential superior therapy, based on the above factors. In some embodiments, however, the classifications remain distinct, such that the user can analyze each class of potential therapies separately.

The method 900 then continues to block 935, where the Therapy Suggestion Application 165 determines whether at least one additional potential therapy remains to be evaluated. If so, the method 900 returns to block 905 to select a next potential therapy. Otherwise, the method 900 continues to block 940. At block 940, the Therapy Suggestion Application 165 presents one or more of the potential therapies to the user. In some embodiments, the Therapy Suggestion Application 165 only presents therapies with a score above a predefined threshold, which may be set by the user. In one embodiment, the Therapy Suggestion Application 165 only presents potential therapies with specific classifications, based on user preference. In other embodiments, the scored and ranked potential therapies are presented in an ordered list, which allows the user to review all of the identified potential therapies and their corresponding score or confidence.

Figure 10:
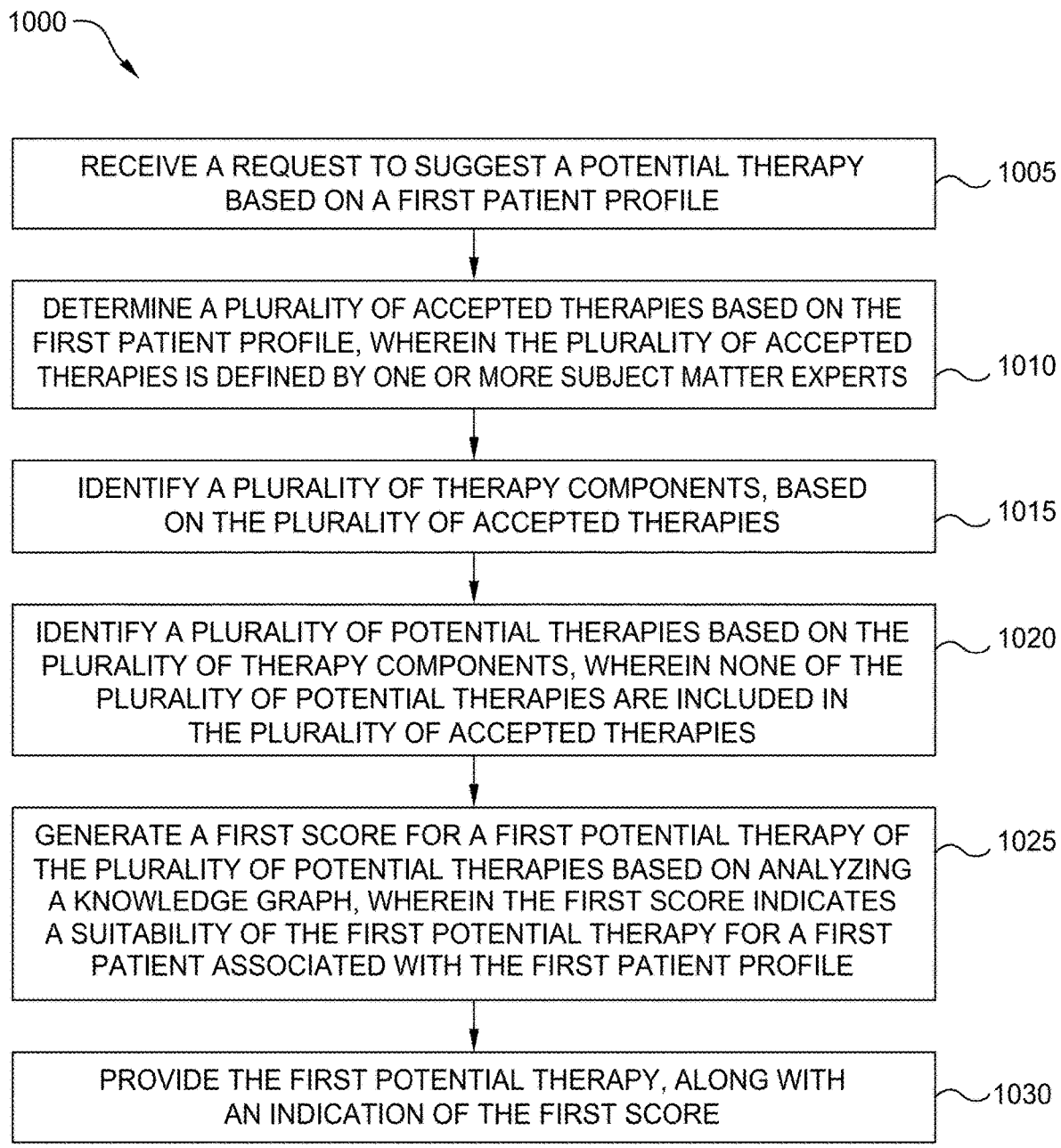
FIG. 10 is a flow diagram illustrating a method for identifying and evaluating potential therapy options, according to one embodiment disclosed herein.

FIG. 10 is a flow diagram illustrating a method 1000 for identifying and evaluating potential therapy options, according to one embodiment disclosed herein. The method 1000 begins at block 1005, where the Therapy Suggestion Application 165 receives a request to suggest a potential therapy based on a first patient profile. At block 1010, the Therapy Suggestion Application 165 determines a plurality of accepted therapies based on the first patient profile, wherein the plurality of accepted therapies is defined by one or more subject matter experts. The method 1000 then proceeds to block 1015, where the Therapy Suggestion Application 165 identifies a plurality of therapy components, based on the plurality of accepted therapies. At block 1020, the Therapy Suggestion Application 165 identifies a plurality of potential therapies based on the plurality of therapy components, wherein none of the plurality of potential therapies are included in the plurality of accepted therapies. The method 1000 then continues to block 1025, where the Therapy Suggestion Application 165 generates a first score for a first potential therapy of the plurality of potential therapies based on analyzing a knowledge graph, wherein the first score indicates a suitability of the first potential therapy for a first patient associated with the first patient profile. Finally, at block 1030, the Therapy Suggestion Application 165 provides the first potential therapy, along with an indication of the first score.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the preceding features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., a Therapy Suggestion Application 165) or related data available in the cloud. For example, the Therapy Suggestion Application 165 could execute on a computing system in the cloud and identify and evaluate potential therapies for patients. In such a case, the Therapy Suggestion Application 165 could evaluate potential therapies, and store generated therapies and efficacy scores at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method comprising:
generating a knowledge graph based at least in part by processing a plurality of documents using one or more natural language processing (NLP) models, wherein:
the knowledge graph comprises a plurality of nodes, each respective node corresponding to a respective therapy, and
the knowledge graph comprises a plurality of edges indicating comparisons between the therapies;
receiving a request to suggest a potential therapy based on a first patient profile;
determining a plurality of accepted therapies based on the first patient profile, wherein the plurality of accepted therapies is based on stored definitions obtained from one or more subject matter experts;

identifying a plurality of therapy components, based on the plurality of accepted therapies, wherein the plurality of therapy components include: (i) one or more medications, (ii) one or more surgical procedures, (iii) one or more activities to partake in, and (iv) one or more activities to refrain from;

identifying a plurality of potential therapies based on the plurality of therapy components, wherein none of the plurality of potential therapies are included in the plurality of accepted therapies;

generating a first score for a first potential therapy of the plurality of potential therapies, by operation of one or more processors, based on analyzing a knowledge graph, wherein the first score indicates a suitability of the first potential therapy for a first patient associated with the first patient profile, comprising:

determining an age of a node, in the knowledge graph, that corresponds to the first potential therapy, wherein the first score is inversely related to the age, and wherein determining the age of the node comprises:

identifying a set of documents that were processed to identify the first potential therapy, and determining a median age of the set of documents;

determining that the first potential therapy has not been directly compared to any of the plurality of accepted therapies; and determining a distance between the first potential therapy and at least one of the plurality of accepted therapies in the knowledge graph, wherein:

the distance corresponds to how many edges in the knowledge graph must be traversed to connect the first potential therapy and at least one of the plurality of accepted therapies, each respective edge in the knowledge graph connects a respective pair of nodes and indicates that a corresponding pair of therapies have been directly compared in at least one document in the plurality of documents, and the first score is inversely related to the distance; and providing the first potential therapy, along with an indication of the first score.

2. The method of claim 1, wherein the plurality of therapy components includes a first therapy component, and wherein identifying the plurality of potential therapies comprises:

identifying one or more therapies that are not included in the plurality of accepted therapies; and determining, for each respective therapy of the one or more therapies not included in the plurality of accepted therapies, whether the respective therapy includes the first therapy component.

3. The method of claim 2, wherein identifying the plurality of potential therapies further comprises:

determining a class of the first therapy component, wherein the first therapy component is a medication; and determining, for each respective therapy of the one or more therapies not included in the plurality of accepted therapies, whether the respective therapy includes a therapy component belonging to the class of the first therapy component.

4. The method of claim 2, wherein identifying the plurality of potential therapies further comprises:

determining one or more broader therapy components that include the first therapy component; and determining, for each respective therapy of the one or more therapies not included in the plurality of accepted therapies, whether the respective therapy includes at least one of the one or more broader therapy components.

5. The method of claim 2, wherein identifying the plurality of potential therapies further comprises:

determining one or more specific therapy components that are included within the first therapy component; and determining, for each respective therapy of the one or more therapies not included in the plurality of accepted therapies, whether the respective therapy includes at least one of the one or more specific therapy components.

6. The method of claim 1, wherein identifying the plurality of potential therapies further comprises classifying each of the plurality of potential therapies as either (i) a potential superior therapy, (ii) a potential alternative therapy, or (iii) a potential new therapy.

7. The method of claim 1, wherein generating the first score for the first potential therapy comprises determining a measure of similarity between the first potential therapy and the plurality of accepted therapies, based on the plurality of therapy components.

8. The method of claim 1, wherein generating the first score for the first potential therapy comprises determining an efficacy of the first potential therapy.

9. The method of claim 1, wherein generating the first score for the first potential therapy comprises:

identifying a first pair-wise comparison in a plurality of pair-wise comparisons that is associated with the first potential therapy and at least one of the plurality of accepted therapies, wherein the plurality of pair-wise comparisons were used to generate the knowledge graph.

10. The method of claim 1, wherein generating the first score for the first potential therapy comprises:

determining a minimum number of pair-wise comparisons in a plurality of pair-wise comparisons that are required connect the first potential therapy to at least one of the plurality of accepted therapies in the knowledge graph.

11. A computer-readable storage medium having computer-readable program code embodied therewith, the computer-readable program code executable by one or more computer processors to perform an operation comprising:

generating a knowledge graph based at least in part by processing a plurality of documents using one or more natural language processing (NLP) models, wherein:

the knowledge graph comprises a plurality of nodes, each respective node corresponding to a respective therapy, and the knowledge graph comprises a plurality of edges indicating comparisons between the therapies;

receiving a request to suggest a potential therapy based on a first patient profile;

determining a plurality of accepted therapies based on the first patient profile, wherein the plurality of accepted therapies is based on stored definitions obtained from one or more subject matter experts;

identifying a plurality of therapy components, based on the plurality of accepted therapies, wherein the plurality of therapy components include (i) one or more medications, (ii) one or more surgical procedures, (iii) one or more activities to partake in, and (iv) one or more activities to refrain from;

identifying a plurality of potential therapies based on the plurality of therapy components, wherein none of the plurality of potential therapies are included in the plurality of accepted therapies;
generating a first score for a first potential therapy of the plurality of potential therapies based on analyzing a knowledge graph, wherein the first score indicates a suitability of the first potential therapy for a first patient associated with the first patient profile, comprising:
determining an age of a node, in the knowledge graph, that corresponds to the first potential therapy, wherein the first score is inversely related to the age, and wherein determining the age of the node comprises:
identifying a set of documents that were processed to identify the first potential therapy, and
determining a median age of the set of documents;
determining that the first potential therapy has not been directly compared to any of the plurality of accepted therapies; and
determining a distance between the first potential therapy and at least one of the plurality of accepted therapies in the knowledge graph, wherein:
the distance corresponds to how many edges in the knowledge graph must be traversed to connect the first potential therapy and at least one of the plurality of accepted therapies,
each respective edge in the knowledge graph connects a respective pair of nodes and indicates that a corresponding pair of therapies have been directly compared in at least one document in the plurality of documents, and
the first score is inversely related to the distance; and
providing the first potential therapy, along with an indication of the first score.

12. The computer-readable storage medium of claim 11, wherein the plurality of therapy components includes a first therapy component, and wherein identifying the plurality of potential therapies comprises:
identifying one or more therapies that are not included in the plurality of accepted therapies; and
determining, for each respective therapy of the one or more therapies not included in the plurality of accepted therapies, whether the respective therapy includes the first therapy component.

13. The computer-readable storage medium of claim 12, wherein identifying the plurality of potential therapies further comprises:
determining a class of the first therapy component, wherein the first therapy component is a medication; and
determining, for each respective therapy of the one or more therapies not included in the plurality of accepted therapies, whether the respective therapy includes a therapy component belonging to the class of the first therapy component.

14. The computer-readable storage medium of claim 12, wherein identifying the plurality of potential therapies further comprises:
determining one or more broader therapy components that include the first therapy component; and
determining, for each respective therapy of the one or more therapies not included in the plurality of accepted therapies, whether the respective therapy includes at least one of the one or more broader therapy components.

15. The computer-readable storage medium of claim 12, wherein identifying the plurality of potential therapies further comprises:
determining one or more specific therapy components that are included within the first therapy component; and
determining, for each respective therapy of the one or more therapies not included in the plurality of accepted therapies, whether the respective therapy includes at least one of the one or more specific therapy components.

16. A system comprising:
one or more computer processors; and
a memory containing a program which when executed by the one or more computer processors performs an operation, the operation comprising:
generating a knowledge graph based at least in part by processing a plurality of documents using one or more natural language processing (NLP) models, wherein:
the knowledge graph comprises a plurality of nodes, each respective node corresponding to a respective therapy, and
the knowledge graph comprises a plurality of edges indicating comparisons between the therapies;
receiving a request to suggest a potential therapy based on a first patient profile;
determining a plurality of accepted therapies based on the first patient profile, wherein the plurality of accepted therapies is based on stored definitions obtained from one or more subject matter experts;
identifying a plurality of therapy components, based on the plurality of accepted therapies, wherein the plurality of therapy components include (i) one or more medications, (ii) one or more surgical procedures, (iii) one or more activities to partake in, and (iv) one or more activities to refrain from;
identifying a plurality of potential therapies based on the plurality of therapy components, wherein none of the plurality of potential therapies are included in the plurality of accepted therapies;
generating a first score for a first potential therapy of the plurality of potential therapies based on analyzing a knowledge graph, wherein the first score indicates a suitability of the first potential therapy for a first patient associated with the first patient profile, comprising:
determining an age of a node, in the knowledge graph, that corresponds to the first potential therapy, wherein the first score is inversely related to the age, and wherein determining the age of the node comprises:
identifying a set of documents that were processed to identify the first potential therapy, and
determining a median age of the set of documents;
determining that the first potential therapy has not been directly compared to any of the plurality of accepted therapies; and
determining a distance between the first potential therapy and at least one of the plurality of accepted therapies in the knowledge graph, wherein:
the distance corresponds to how many edges in the knowledge graph must be traversed to connect the first potential therapy and at least one of the plurality of accepted therapies,
each respective edge in the knowledge graph connects a respective pair of nodes and indicates that a corresponding pair of therapies have been directly compared in at least one document in the plurality of documents, and the first score is inversely related to the distance; and providing the first potential therapy, along with an indication of the first score.

17. The system of claim 16, wherein the plurality of therapy components includes a first therapy component, and wherein identifying the plurality of potential therapies comprises:

identifying one or more therapies that are not included in the plurality of accepted therapies; and determining, for each respective therapy of the one or more therapies not included in the plurality of accepted therapies, whether the respective therapy includes the first therapy component.

18. The system of claim 17, wherein identifying the plurality of potential therapies further comprises:

determining a class of the first therapy component, wherein the first therapy component is a medication; and determining, for each respective therapy of the one or more therapies not included in the plurality of accepted therapies, whether the respective therapy includes a therapy component belonging to the class of the first therapy component.

19. The system of claim 17, wherein identifying the plurality of potential therapies further comprises:

determining one or more broader therapy components that include the first therapy component; and determining, for each respective therapy of the one or more therapies not included in the plurality of accepted therapies, whether the respective therapy includes at least one of the one or more broader therapy components.

20. The system of claim 17, wherein identifying the plurality of potential therapies further comprises:

determining one or more specific therapy components that are included within the first therapy component; and determining, for each respective therapy of the one or more therapies not included in the plurality of accepted therapies, whether the respective therapy includes at least one of the one or more specific therapy components.

\* \* \* \* \*